US008343746B2

(12) United States Patent
Rank et al.

(10) Patent No.: US 8,343,746 B2
(45) Date of Patent: Jan. 1, 2013

(54) POLYMERASE ENZYMES AND REAGENTS FOR ENHANCED NUCLEIC ACID SEQUENCING

(75) Inventors: David R. Rank, Palo Alto, CA (US);
Arek Bibillo, Cupertino, CA (US); Paul Peluso, Hayward, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 53 days.

(21) Appl. No.: 11/977,160

(22) Filed: Oct. 22, 2007

(65) Prior Publication Data

US 2008/0108082 A1    May 8, 2008

Related U.S. Application Data

(60) Provisional application No. 60/853,939, filed on Oct. 23, 2006.

(51) Int. Cl.
*C12N 9/12* (2006.01)
*C12P 19/34* (2006.01)

(52) U.S. Cl. ......................... 435/194; 435/183; 435/91.1

(58) Field of Classification Search .......................... None
See application file for complete search history.

(56) References Cited

U.S. PATENT DOCUMENTS

| | | | |
|---|---|---|---|
| 5,001,050 A | 3/1991 | Blanco et al. | |
| 5,198,543 A * | 3/1993 | Blanco et al. | 536/23.2 |
| 5,576,204 A | 11/1996 | Blanco et al. | |
| 5,998,580 A | 12/1999 | Fay et al. | |
| 6,607,883 B1 * | 8/2003 | Frey et al. | 435/6 |
| 6,767,704 B2 | 7/2004 | Waldman et al. | |
| 6,917,726 B2 | 7/2005 | Levene et al. | |
| 7,033,764 B2 | 4/2006 | Korlach et al. | |
| 7,041,812 B2 * | 5/2006 | Kumar et al. | 536/23.1 |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,361,466 B2 | 4/2008 | Korlach et al. | |
| 7,405,281 B2 | 7/2008 | Xu et al. | |
| 7,476,504 B2 * | 1/2009 | Turner | 435/6.12 |
| 2001/0031483 A1 | 10/2001 | Sorge et al. | |
| 2003/0036181 A1 | 2/2003 | Okkels et al. | |
| 2003/0044781 A1 | 3/2003 | Korlach et al. | |
| 2003/0087315 A1 | 5/2003 | Prockop et al. | |
| 2003/0121854 A1 | 7/2003 | Reis | |
| 2003/0140369 A1 | 7/2003 | Simmons | |
| 2003/0152988 A1 | 8/2003 | Gelfand et al. | |
| 2004/0018969 A1 | 1/2004 | Rosen et al. | |
| 2004/0259082 A1 | 12/2004 | Williams | |
| 2005/0009189 A1 | 1/2005 | Lechelt-Kunze et al. | |
| 2005/0042633 A1 | 2/2005 | Williams | |
| 2005/0187718 A1 | 8/2005 | Edwards et al. | |
| 2007/0196846 A1 | 8/2007 | Hanzel et al. | |

FOREIGN PATENT DOCUMENTS

| | | |
|---|---|---|
| WO | WO 00/53805 A1 | 9/2000 |
| WO | WO 02/86088 A2 | 10/2002 |
| WO | WO 2007/076057 A2 | 7/2007 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Bernad et al. (2006) "The Highly Conserved Amino Acid Sequence Motif Tyr-Gly-Asp-Thr-Asp-Ser in α-like DNA Polymerases is Required by Phage φ29 DNA Polymerase for Protein-primed Initiation of Polymerization." Proceedings of the National Academy of Sciences, USA, 87(12): 4610-4614.
Blanco et al. (1995) "Mutational Analysis of Bacteriophage Phi 29 DNA Polymerase." *Methods of Enzimol.* 262: 283-294.
Blasco et al. (1990) "Structural and Functional Analysis of Temperature-sensitive Mutants of the Phage φDNA Polymerase." Nucleic Acids Research, 18(16): 4763-4770.
Blasco et al. (1992) "Primer Terminus Stabilization at the φ29 DNA Polymerase Active Site." The Journal of Biological Chemistry, 270(6): 2735-2740.
Blasco et al. (1992) "Structural and Functional Studies on φ29 DNA Polymerase." Chromosoma, 102: S32-S38.
Blasco et al. (1993) "Phi 29 DNA Polymerase Active Site. Residue ASP249 of Conserved Amino Acid Motif 'Dx2SLYP' is Critical for Synthetic Activities." *J. Biol Chem.*, 268(32): 24106-13.
Blaso et al. (1993) "Phi 29 DNA Polymerase Active Site. The Conserved Amino Acid Motif 'Kx3NSxYG' is Involved in Template-primer Binding and dNTP Selection." *The Journal of Biological Chemistry*, 268(22): 16763-16770.
Bonnin et al. (1999) "A Single Tyrosine Prevents Insertion of Ribonucleotides in the Eukaryotic-type φ29 DNA Polymerase." The Journal of Molecular Biology, 290: 241-251.
Brueggemeier et al. (2003) "Protein-acrylamide Copolymer Hydrogels for Array-based Detection of Tyrosine Kinase Activity from Cell Lysates." *Biomacromolecules*, 6(5): 2765-2775.
Burgers et al. (2001) "Eukaryotic DNA Polymerases: Proposal for a Revised Nomenclature." *The Journal of Biological Chemistry*, 276(47): 43487-43490. Defour et al. (2000) "An Aspartic Acid Residue in TPR-1, a Specific Region of Protein-priming DNA Polymerase, is Required for the Functional Interaction with Primer Terminal Protein." *The Journal of Molecular Biology*, 304: 289-300.
Defour et al. (2003) "A Conserved Insertion in Protein-primed DNA Polymerases is Involved in Primer Terminus Stabilisation." *The Journal of Molecular Biology*, 331: 781-794.
DeVega et al. (1996) "Primer-terminus Stabilization at the 3'-5' Exonuclease Active Site of φ29 DNA Polymerase. Involvment of Two Amino Acid Residues Highly Conserved in Proofreading DNA Polymerases." The EMBO Journal, 15(5): 1182-1192.
DeVega et al. (1997) "An Invariant Lysine Residue is Involved in Catalysis at the 3'5' Exonuclease Active Site of Eukaryotic-type DNA Polymerase." *The Journal of Molecular Biology*, 270: 65-78.

(Continued)

*Primary Examiner* — Richard Hutson
(74) *Attorney, Agent, or Firm* — Quine Intellectual Property Law Group, P.C.; Monica Elrod-Erickson; Robert Reamey

(57) ABSTRACT

Compositions that include DNA polymerases having increased residence times for nucleotide analogues, particularly modified recombinant Φ29-type DNA polymerases with such increased residence times, are provided. Methods of making the polymerases and of using the polymerases in sequencing and DNA amplification are also provided. Compositions including α-thiophosphate nucleotide analogues with four or more phosphate groups are described, as are methods for determining the sequence of nucleic acid molecules using such analogues.

25 Claims, 5 Drawing Sheets

OTHER PUBLICATIONS

DeVega et al. (1998) "Mutational Analysis of φ29 DNA Polymerase Residues Acting as ssDNA Ligands for 3'-5' Exonucleoysis." The Journal of Molecular Biology, 279: 807-822.

DeVega et al. (1998) "φ29 DNA Polymerase Residue Ser122, a Single-stranded DNA Ligand for 3'-5' Exonucleoysis, Is Required to Interact with the Terminal Protein." The Journal of Biological Chemistry, 273(44): 28966-28977.

DeVega et al. (1999) "Processive Proofreading and the Spatial Relationship between Polymerase and Exonuclease Active Sites of Bacteriophage φ29 DNA Polymerase." The Jounral of Molecular Biology, 292: 39-51.

DeVega et al. (2000) "Phage φ29 DNA Polymerase Residues Involved in the Proper Stabilisation of the Primer-terminus at the 3'-5' Exonuclease Active Site." The Journal of Molecular Biology, 304: 1-9.

Eisenbrandt et al. (2002) "φ29 DNA Polymerase Residue Try59, His61 and Phe69 of the Hihgly Conserved ExoII Motif are Essential for Interaction with the Terminal Protein." Nucleic Acids Research, 30(6): 1379-1386.

Esteban et al. (1993) "Fidelity of φ29 DNA Polymerase." The Journal of Biological Chemistry, 268(4): 2719-2726.

Esteban et al. (1994) "3'—>5' Exonuclease Active Site of Phi DNA Polymerase. Evidence Favoring a Metal Ion-assisted Reaction Mechanims." *The Journal of Biological Chemistry*, 269(5): 31946-31954.

Gardner and Jack (1999) "Determinants of Nucleotide Sugar Recognition in an Archaean DNA Polymerase." *Nucleid Acids Research*, 27(12): 2545-2553.

Gardner et al. (2004) "Comparative Kinetics and Nucleotide Analog Incorporation by Vent DNA Polymerase." *The Journal of Biological Chemistry*, 279(12): 11834-11842.

Giller et al. (2003) "Incorporation of Reporter Molecule-labeled Nucleotides by DNA Polymerases. I. Chemical Synthesis of Various Reporter Group-labeled 2'-deoxyribonucleoside-5'-triphosphates." *Nucleic Acids Research*, 31(10): 2630-2635.

Hubscher et al. (2002) "Eukaryotic DNA Polymerases." *Annual Review of Biochemistry*, 71: 133-163.

Illana et al. (1998) "The RGD Sequence in Phage φ29 Terminal Protein is Required for Interaction with φ29 DNA Polymerase." Virology, 248: 12-19.

Illana et al. (1999) "Phage φ29 Terminal Protein Residues Asn80 and Try82 are Recognition Elements of the Replication Origins." The Journal of Biological Chemistry, 274(21): 15073-15079.

Inoue et al. (2006) "Improvements of Rolling Circle Amplification (RCA) Efficiency and Accuracy Using *Thermus thermophilus* SSB Mutant Protein." *Nucleic Acids Research*, 34(9): e69.

Kamtekar et al. (2004) "Insights into Strand Displacement and Processivity from the Crystal Structure of the Proetin-prined DNA Polymerase of Bacteriophage φ29." Molecular Cell, 16: 609-618.

Kamtekar et al. (2006) "The φ29 DNA Polymerase Protein-primer Structure Suggests a Model for the Initiation to Elongation Transition." The EMBO Journal, 25(6): 1335-1343.

Levene et al. (2003) "Zero-mode Waveguides for Single-molecule Analysis at High Concentrations." *Science*, 299(5607): 682-686.

Longas et al. (2006) "Functional Characterization of Highly Processive Protein-primed DNA Polymerase from Phages Nf and GA-1, Endowed with a Potent Strand Displacement Capacity." *Nucleic Acids Research*, 34(20): 6051-6063.

Meijer et al. (2002) "Phi 29 Family of Phages." *Microbiology and Molecular Biology Reviews*, 65(2): 261-287.

Mendez et al. (1994) "Primer-terminus Stablization at the φ29 DNA Polymerase Active Site." The Journal of Biological Chemistry, 269(47): 30030-30038.

Mendez et al. (1997) "Protein-primed DNA Replication: a Transition Between Two Modes of Priming by a Unique DNA Polymerase." *The EMBO Journal*, 16(9): 2519-2527.

Nieba et al. (1997) "BIACORE Analysis of Histidine-tagged Proteins Using a Chelating NTA Sensor Chip." *Analytical Biochemistry*, 252: 217-228.

Nilsson et al. (1997) "Heat-mediated Activation of Affinity-immobilized Taq DNA Polymerase." *BioTechniques* 22(4): 744-751.

Ried et al. (1992) "Simultaneous Visualization of Seven Different DNA Probes by in Situ Hybridization Using Combinatorial Fluorescence and Digital Imaging Microscopy." *Proceedings of the National Academy of Sciences*, USA, 89(4): 1388-1392.

Rodriguez et al. (2003) "φ29 DNA Polymerase Residue Phe128 of the Highly Conserved (S/T)Lx2h Motif is Required for a Stable and Functional Interaction with the Termial Protein." The Journal of Molecular Biology, 325: 85-97.

Rodriguez et al. (2004) "φ29 DNA Polymerase—Terminal Protein Interaction, Involvement of Residues Specifically Conserved Among Protein-primed DNA Polymerases." The Journal of Molecular Biology, 337: 829-841.

Rodriguez et al. (2005) "A Specific Subdomain in φ29 DNA Polymerase Confers Both Processivity and Strand-displacement Capacity." The Proceedings of the National Academy of Sciences, USA, 102: 6407-6412.

Saturno et al. (1997) "φ29 DNA Polymerase as a Residue Lys383, Invariant at Motif B of DNA-dependent Polymerases, is Involved in dNTP Binding." The Journal of Molecular Biology, 269: 313-325.

Saturno et al. (1998) "Role of the First Asparate Residue of the 'YxDTDS' Motif of φ29 DNA Polymerase as a Metal Ligand During Both TP-primed and DNA-primed DNA Synthesis." The Journal of Molecular Biology, 283: 633-642.

Soengas et al. (1992) "Site-directed Mutagenesis at the Exo III Motif of φ29 DNA Polymerase; Overlapping and Strand-Displacement Activities." The EMBO Journal, 11(11): 4227-4237.

Steitz (1999) "DNA Polymerases: Structural Diversity and Common Mechanisms." *The Journal of Biological Chemistry*, 274(25): 17395-17398.

Steitz (2006) "Visualizing Polynucleotide Polymerase Machines at Work." *The EMBO Journal*, 25(15): 3458-3468.

Tonon et al. (2000) "Spectral Karyotyping Combined with Locus-specific FISH Simultaneously Defines Genes and Chromosomes Involved in Chromosomal Translocations." *Genes, Chromosomes & Cancer*, 27: 418-423.

Truniger et al. (2003) "φ29 DNA Polymerase Residue Leu384, Highly Conserved in Motif B of Eukaryotic Type DNA Replicases, Is Involved in Nucleotide Insertion Fidelity." The Journal of Biological Chemistry, 278(35): 33482-33491.

Truniger et al. (2004) "Function of the C-terminus of φ29 DNA Polymerase in DNA and Terminal Protein Binding." Nucleic Acids Research, 32(1): 361-370.

Truniger et al. (2004) "Two Positively Charged Residues of φ29 DNA Polymerase, Conserved in Protein-primed DNA Polymerases, are Involved in Stabilisation of the Incoming Nucleotide." The Journal of Molecular Biology, 335(2): 481-494.

Truniger et al. (2005) "Involvement if the 'Linker' Region Between the Exonuclease and Polymerization Domains of φ29 DNA Polymerase in DNA and TP Binding." Gene, 348: 89-99.

Yu et al. (1994) "Cyanine dye dUTP Analogs for Enzymatic Labeling of DNA Probes." *Nucleic Acids Research*, 22(15): 3226-3232.

Zhu and Waggoner (1997) "Molecular Mechanism Controlling the Incorporation of Fluorescent Nucleotides into DNA by PCR." *Cytometry*, 28: 206-211.

Zhu et al. (1994) "Directly Labeled DNA Probes Using Fluorescent Nucleotides with Different Length Linkers." *Nucleic Acids Research*, 22(16): 3418-3422.

Benkovic and Schray (1973) "Chemical basis of biological phosphoryl transfer," in *The Enzymes*, Boyer (ed), 8:201-238, Academic Press, New York.

Eger and Benkovic (1992) "Minimal kinetic mechanism for misincorporation by DNA polymerase I (Klenow fragment)," *Biochemistry*, 31(38):9227-9236.

Mizrahi et al. (1985) "Rate-limiting steps in the DNA polymerase I reaction pathway," *Biochemistry*, 24(15):4010-4018.

Patel et al. (1991) "Pre-steady-state kinetic analysis of processive DNA replication including complete characterization of an exonuclease-deficient mutant" Biochemistry 30(2):511-525.

Tsai and Johnson (2006) "A new paradigm for DNA polymerase specificity," *Biochemistry*, 45(32):9675-9687.

Zakharova et al. (2004) "The Activity of Selected RB69 DNA Polymerase Mutants Can Be Restored by Manganese Ions: The Existence of Alternative Metal Ion Ligands Used during the Polymerization Cycle," *Biochemistry*, 43(21):6587-6595.

Bernad et al. (1990) "The highly conserved amino acid sequence motif Tyr-Gly-Asp-Thr-Asp-Ser in alpha-like DNA polymerases is required by phage phi 29 DNA polymerase for protein-primed initiation and polymerization." pnas, 87(12): 4610-4614.

De Vega et al. (1996) "Primer-terminus stabilization at the 3'-5' exonuclease active site of phi29 DNA polymerase. Involvement of two amino acid residues highly conserved in proofreading DNA polymerases." EMBO Journal, 15(5): 1182-1192.

De Vega et al. (1998) Phi 29 DNA Polymerase residue SER122, a single-stranded DNA ligand for 3'-5' exonucleolysis, is required to interact with the terminal protein. J. Biol. Chem. 273(44): 28966-28977.

Meijer et al. (2001) "Phi 29 Family of Phages." Microbiology and Molecular Biology Reviews, 65: 261-287.

Miyazaki et al. (2005) Efficient Immobilization of Enzymes on Microchannel Surface Through His-Tag and Applications for Microreactor. Protein and Peptide Letters, 12(2): 207-210.

Salas et al. (1990) "Structure and function of the bacteriophage phi-29 replication proteins," Molecular Mechanisms in DNA Replication and Recombination, v.127, pp. 277-288.

Blanco and Salas (1996) "Relating Structure to Function in φ29 DNA Polymerase." The Journal of Biological Chemistry, 271(15): 8509-8512.

Blasco et al. (1992) "φ29 DNA Polymerase Active Site." The Journal of Biological Chemistry, 267(27): 19427-19434.

Blasco et al. (1992) "φ29 DNA Polymerase Active Site." The Journal of Biological Chemistry, 268(32): 24106-24113.

Perex-Arnaiz et al. (2006) "Involvement of φ29 DNA Polymerase Thumb Subdomain in the Proper Coordination of Synthesis and Degradation During DNA Replication." Nucleic Acids Research, 34(10): 3170-3115.

Saturno et al. (1995) "A Novel Kinetic Analysis to Calculate Nucleotide Affinity of Proofreading DNA Polymerases." *The Jounal of Biological Chemistry*, 270(52): 31235-31243.

Truniger et al. (2002) "A Positively Charged Residue of φ29 DNA Polymerase, Highly Conserved in DNA Polymease from Families A and B, is Involved in Binding the Incoming Nucleotide." Nucleic Acids Research, 30(7): 1483-1492.

Adelman et al. (2002) "Single Molecule Analysis of RNA Polymerase Elongation Reveals Uniform Kinetic Behavior." *Proceedings of the National Academy of Sciences*, USA, 99(21): 13538-13543.

Alba (2001) "Protein Family Review: Replicative DNA Polymerases." *Genome Biology* 2(1): reviews 3002.1-3002.4.

Albert et al. (2005) "Structural Basis of Mambrane Anchorage of Viral φ29 DNA During Replication." The Journal of Biological Chemistry, 280(52): 42486-42488.

Augustin et al. (2001) "Progress Towards Single-molecule Sequencing: Enzymatic Synthesis of Nucleotide-specifically Labeled DNA." *Journal of Biotechnology*, 86(3): 289-301.

* cited by examiner

US 8,343,746 B2

POLYMERASE ENZYMES AND REAGENTS FOR ENHANCED NUCLEIC ACID SEQUENCING

CROSS-REFERENCE TO RELATED APPLICATIONS

This application is a non-provisional utility patent application claiming priority to and benefit of the following prior provisional patent application: U.S. Ser. No. 60/853,939, filed Oct. 23, 2006, entitled "POLYMERASE ENZYMES AND REAGENTS FOR ENHANCED NUCLEIC ACID SEQUENCING" by David R. Rank et al., which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. R01-HG003710 from the National Human Genome Research Institute. The government may have certain rights to this invention.

FIELD OF THE INVENTION

The present invention relates to DNA polymerase enzymes and/or nucleotides or nucleotide analogues that provide altered residence times to provide enhanced properties for use in analytical operations, such as nucleic acid sequence analysis and determination. The enzymes and/or nucleotides may have increased or decreased residence times for the interaction of the nucleotides with the enzymes depending upon the desired application. The invention also relates to methods for determining the sequence of nucleic acid molecules using such polymerases and/or the nucleotides described herein.

BACKGROUND OF THE INVENTION

DNA polymerases replicate the genomes of living organisms. In addition to this central role in biology, DNA polymerases are also ubiquitous tools of biotechnology. They are widely used, e.g., for reverse transcription, amplification, labeling, and sequencing, which are central technologies for a variety of applications such as nucleic acid sequencing, nucleic acid amplification, cloning, protein engineering, diagnostics, molecular medicine and many other technologies.

Because of the significance of DNA polymerases, they have been extensively studied. This study has focused, e.g., on phylogenetic relationships among polymerases, structure of polymerases, structure-function features of polymerases, and the role of polymerases in DNA replication and other basic biology, as well as ways of using DNA polymerases in biotechnology. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; Steitz (1999) "DNA polymerases: structural diversity and common mechanisms" J Biol Chem 274:17395-17398 and Burgers et al. (2001) "Eukaryotic DNA polymerases: proposal for a revised nomenclature" J Biol Chem. 276(47):43487-90. Crystal structures have been solved for many polymerases, which often share a similar architecture. The basic mechanisms of action for many polymerases have been determined.

A fundamental application of DNA technology involves various labeling strategies for labeling a DNA that is produced by a DNA polymerase. This is useful in DNA sequencing, microarray technology, SNP detection, cloning, PCR analysis, and many other applications. Labeling is often performed in various post-synthesis hybridization or chemical labeling schemes, but DNA polymerases have also been used to directly incorporate various labeled nucleotides in a variety of applications, e.g., via nick translation, reverse transcription, random priming, amplification, the polymerase chain reaction, etc. See, e.g., Giller et al. (2003) "Incorporation of reporter molecule-labeled nucleotides by DNA polymerases. I. Chemical synthesis of various reporter group-labeled 2'-deoxyribonucleoside-5'-triphosphates" Nucleic Acids Res. 31(10): 2630-2635; Augustin et al. (2001) "Progress towards single-molecule sequencing: enzymatic synthesis of nucleotide-specifically labeled DNA" J. Biotechnol., 86:289-301; Tonon et al. (2000) "Spectral karyotyping combined with locus-specific FISH simultaneously defines genes and chromosomes involved in chromosomal translocations" Genes Chromosom. Cancer 27:418-423; Zhu and Waggoner (1997) "Molecular mechanism controlling the incorporation of fluorescent nucleotides into DNA by PCR." Cytometry, 28:206-211; Yu et al. (1994) "Cyanine dye dUTP analogs for enzymatic labeling of DNA probes" Nucleic Acids Res., 22:3226-3232; Zhu et al. (1994) "Directly labeled DNA probes using fluorescent nucleotides with different length linkers" Nucleic Acids Res. 22:3418-3422; and Ried et al. (1992) "Simultaneous visualization of seven different DNA probes by in situ hybridization using combinatorial fluorescence and digital imaging microscopy" Proc. Natl. Acad. Sci. USA, 89:1388-1392.

DNA polymerase mutants have been identified that have altered nucleotide analogue incorporation properties relative to wild-type counterpart enzymes. For example, Vent$^{A488L}$ DNA polymerase can incorporate certain non-standard nucleotides with a higher efficiency than native Vent DNA polymerase. See Gardner et al. (2004) "Comparative Kinetics of Nucleotide Analog Incorporation by Vent DNA Polymerase" J. Biol. Chem., 279(12), 11834-11842 and Gardner and Jack "Determinants of nucleotide sugar recognition in an archaeon DNA polymerase" Nucleic Acids Research, 27(12) 2545-2553. The altered residue in this mutant, A488, is predicted to be facing away from the nucleotide binding site of the enzyme. The pattern of relaxed specificity at this position roughly correlates with the size of the substituted amino acid side chain and affects incorporation by the enzyme of a variety of modified nucleotide sugars.

The ability to improve features of DNA polymerases towards labeled nucleotide analogues would be highly desirable in a variety of contexts where, e.g., nucleic acid labeling is desired, including DNA sequencing, amplification, labeling, detection, cloning, and many others. The present invention provides new DNA polymerases with modified properties for labeled nucleotide analogues, methods of making such polymerases, methods of using such polymerases, particularly in nucleic acid sequencing, and many other features that will become apparent upon a complete review of the following.

SUMMARY OF THE INVENTION

The invention is generally directed to modified or engineered compositions that are characterized by increased retention times for polymerase-nucleotide interactions during template dependent incorporation of nucleotides. In particular, the invention provides one or more of engineered or modified polymerase enzymes and/or engineered or modified nucleotides or nucleotide analogues, where the composition including such polymerase and/or nucleotide or nucleotide analogue exhibits an increased time of retention of the nucleotide or nucleotide analogue by the polymerase when the nucleotide or nucleotide analogue is incorporated by the polymerase enzyme during template dependent polymerase mediated nucleic acid synthesis.

Thus, in at least a first aspect, the invention includes polymerases that incorporate nucleotide analogues into growing template copies during template dependent, polymerase mediated nucleic acid synthesis. The polymerases are typically selected, engineered, and/or modified to have increased residence times for the analogues. Such polymerases are particularly well-suited for DNA synthesis, amplification, and/or sequencing applications, particularly sequencing protocols that include detection of incorporation of labeled analogues into DNA amplicons in real time, since the increased residence times facilitate discrimination of nucleotide incorporation events from non-incorporation events such as transient binding of a mis-matched nucleotide.

Alternatively and/or additionally, the invention also provides nucleotides or nucleotide analogues that are selected, engineered and/or modified such that they will yield longer retention times by an employed polymerase enzyme, as compared to a naturally occurring nucleotide, or labeled naturally occurring nucleoside triphosphate. For example, in at least one preferred aspect, the invention relates to use of α-thiophosphate nucleotide analogues in sequencing applications. Without being bound to a particular theory of operation, it is believed that the α-thio substitution in the analogues slows incorporation of the nucleotides, again facilitating discrimination of nucleotide incorporation events from non-incorporation events in real-time sequencing applications.

Accordingly, in one aspect, the invention includes a composition that comprises a modified or engineered recombinant Φ29-type DNA polymerase. The modified recombinant Φ29-type polymerases of the invention typically exhibit a residence time for a nucleotide analogue that is greater than a residence time for the nucleotide analogue exhibited by a corresponding wild-type polymerase. The polymerase is optionally a recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase.

The modified recombinant polymerase generally comprises at least one mutation (e.g., one or more amino acid substitutions, insertions, or deletions) relative to the wild-type enzyme that increase residence time, and will typically include more substantial modifications over conventional or wild-type Φ29 type polymerases, including the addition of fusion peptides, insertions, deletions, or the like. Without being bound to any particular theory of operation, such mutations that increase residence time include, for example, mutations that stabilize the closed conformation of the recombinant polymerase. In one class of embodiments, the modified recombinant polymerase comprises one or more amino acid substitutions at one or more positions selected from the group consisting of position 135, position 368, position 372, position 478, position 480, and position 512, wherein numbering of positions is relative to wild-type Φ29 polymerase. For example, the modified recombinant polymerase optionally comprises one or more amino acid substitutions selected from the group consisting of: K135D, K135E, T368D, T368E, T372D, T372E, T372R, T372K, K478D, K478E, K478R, L480K, L480R, K512D, and K512E. Exemplary modified recombinant Φ29 type polymerases of the invention include at least one amino acid substitution or combination of substitutions selected from the group consisting of K135D, K135E, K512D, K512E, T372D, T372E, L480K, L480R, T368D and L480K, T368E and L480K, T372D and K478R, T372E and K478R, T372R and K478D, T372R and K478E, T372K and K478D, and T372K and K478E.

The polymerase optionally further includes one or more mutations relative to the wild-type polymerase that reduce or eliminate endogenous exonuclease activity. For example, relative to the wild-type Φ29 DNA polymerase, N62 is optionally mutated or deleted to reduce exonuclease activity; e.g., the polymerase can include an N62D mutation. Other exemplary mutations that reduce exonuclease activity include D12A, T15I, E14I, and D66A; accordingly, the polymerases of the invention optionally comprise one or more of these mutations. Similarly, the modified recombinant DNA polymerase optionally includes additional features exogenous or heterologous to a corresponding DNA polymerase such as a wild-type or nuclease deficient polymerase. For example, the modified recombinant polymerase optionally includes one or more exogenous affinity tags, e.g., purification or substrate binding tags.

As noted, the modified recombinant polymerase exhibits a residence time for a nucleotide analogue that is greater than that of a corresponding wild-type polymerase. For example, the residence time of the modified recombinant polymerase for the nucleotide analogue is at least about 1.5 times that of the corresponding wild type polymerase, and in many cases is optionally between about 1.5 and about 4 times (e.g., between about 1.5 and about 3 times or between about 1.5 and about 2.5 times) the residence time of the corresponding wild-type polymerase for the nucleotide analogue. The residence time of the modified recombinant polymerase for the nucleotide analogue is typically greater than about 20 msec, and preferably between about 20 msec and about 300 msec when operating under typical template replication conditions. In one class of embodiments, the residence time of the modified recombinant polymerase for the nucleotide analogue is between about 55 msec and about 100 msec.

The composition optionally includes the nucleotide analogue, which may or may not additionally be modified to enhance its retention time with the subject polymerase enzyme, as described elsewhere herein. Exemplary nucleotide analogues include those that include fluorophore and/or dye moieties. Such labeled nucleotide analogues can be, e.g., base, sugar and/or phosphate-labeled nucleotide analogues, including mono-deoxy phosphate-labeled nucleotide analogues and/or dideoxy phosphate-labeled nucleotide analogues. One example class of nucleotide analogues includes analogues having from 3 to 6 phosphate groups (e.g., where the nucleotide analogue is a triphosphate, a tetraphosphate, a pentaphosphate or a hexaphosphate). Thus, for example, the nucleotide analogue can be a labeled nucleotide analogue having from 3 to 6 phosphate groups, e.g., an analogue labeled with a fluorophore on the terminal phosphate. The analogue residue that is incorporated into a growing polynucleotide by the polymerase can be the same as a natural residue, e.g., where a label or other moiety of the analogue is removed by action of the polymerase during incorporation, or the analogue residue can have one or more feature that distinguishes it from a natural nucleotide residue.

It will be evident that the modified recombinant polymerase can exhibit an increased residence time for more than one nucleotide analogue (e.g., for two, three, four, or more analogues), and the composition optionally includes two, three, four, or more nucleotide analogues (e.g., four analogues that represent analogous compounds to the four natural nucleotides, A, T, G and C). For example, the composition optionally includes two, three, four, or more labeled nucleotide analogues bearing detectably different labels (e.g., fluorophores with different emission and/or absorption characteristics) and for which the modified recombinant polymerase exhibits increased residence times as compared to the corresponding wild-type polymerase.

The nucleotide analogue(s) and a DNA template are optionally included in compositions of the invention, e.g., in which the modified recombinant polymerase incorporates the nucleotide analogue(s) into a copy nucleic acid in response to the template DNA. The template DNA can be amplified and/or sequenced. Thus, the composition can be present in a DNA amplification and/or sequencing system. Optionally, in one class of embodiments, the composition is present in a DNA sequencing system comprising a zero mode waveguide.

Methods of making and using the compositions are also features of the invention. For example, in one aspect, methods of synthesizing nucleic acids, such as a DNA, e.g., comprising one or more nucleotide analogue residues, are provided. In these methods, a reaction mixture is provided. The reaction mixture typically includes those components that can at least partially replicate a template, e.g., a template, one or more nucleotides and/or nucleotide analogues, a polymerase, and a replication initiating moiety that complexes with the template, or is integral to it, to prime the polymerase. The replication initiating moiety in this context is any moiety that can serve as a site to initiate the polymerase, e.g., a separate oligonucleotide complementary to the template, a hairpin or other self-complementary region of a template (e.g., a hairpin in a single-stranded template), a terminal protein, or the like. The polymerase is a modified recombinant Φ29-type polymerase capable of at least partially replicating the template in a template-dependent polymerase extension reaction (e.g., using the replication initiation moiety as a site of initiation), and the polymerase exhibits a residence time for a first nucleotide analogue that is greater than a residence time for the first nucleotide analogue exhibited by a corresponding wild-type polymerase. The one or more nucleotides and/or analogues provided in the reaction mixture comprise the first nucleotide analogue (and optionally also a second, third, fourth, etc. nucleotide analogue for which the polymerase also has an increased residence time).

The mixture is reacted such that the modified recombinant polymerase replicates at least a portion of the template in a template-dependent manner, whereby the one or more nucleotides and/or nucleotide analogues (including the first and optional second, third, fourth, etc. analogues) are incorporated into the resulting DNA. Incorporation of an analogue can result in the incorporation of a non-standard residue into the extended DNA (e.g., as a labeled nucleotide residue), or action of the polymerase can modify the analogue such that the nucleotide analogue residue incorporated into the extended DNA is structurally the same as a standard nucleotide residue. For example, in the latter embodiment, a variety of labels are cleaved by action of the polymerase, e.g., certain phosphate labels discussed in more detail herein, are cleaved from the nucleotide analogue as it is incorporated into the growing DNA.

The mixture is optionally reacted in a zero mode waveguide, e.g., for observation of individual polymerase molecules and detection of incorporation of nucleotides and/or analogues by the molecule. Thus, in one embodiment, the methods include detecting incorporation of the first (and optional second, third, fourth, etc.) nucleotide analogue, for example, in applications such as sequencing.

The polymerases used in the methods can be any of those noted above with reference to the compositions. The properties of the polymerases used in the methods can be any of those noted in reference to compositions. For example, the modified recombinant polymerase typically has a residence time for the first (and optional second, third, fourth, etc.) nucleotide analogue of greater than about 20 msec, and optionally between about 20 msec and about 300 msec when operating under typical template replication conditions. In one class of embodiments, the residence time of the modified recombinant polymerase for the nucleotide analogue is between about 55 msec and about 100 msec. Similarly, the nucleotide analogues used in the methods can be any of those noted in reference to the compositions herein. For example, the first (and/or optional second, third, fourth, etc.) nucleotide analogue can be a phosphate-labeled nucleotide analogue and/or a labeled nucleotide analogue having from 3-6 phosphate groups.

As noted above, modified recombinant polymerases with increased residence times for nucleotide analogues are particularly useful in DNA sequencing protocols in which incorporation of labeled analogues into DNA amplicons is monitored in real time, since the increased residence times facilitate discrimination of nucleotide incorporation events from non-incorporation events, thereby reducing the possibility of sequencing errors.

Accordingly, one aspect of the invention provides methods of sequencing a DNA template. In the methods, a reaction mixture is provided that comprises the DNA template, a replication initiating moiety that complexes with or is integral to the template, a modified or engineered recombinant DNA polymerase, and one or more nucleotides and/or nucleotide analogues. The recombinant polymerase is capable of replicating at least a portion of the template using the moiety in a template-dependent polymerization reaction, and the polymerase exhibits a residence time for a first nucleotide analogue that is greater than a residence time for the first nucleotide analogue exhibited by a corresponding wild-type polymerase. The first nucleotide analogue is included in the nucleotides and/or analogues in the reaction mixture. The reaction mixture is subjected to a polymerization reaction in which the recombinant polymerase replicates at least a portion of the template in a template-dependent manner, whereby the one or more nucleotides and/or nucleotide analogues are incorporated into the resulting DNA. To determine the sequence of the template, a time sequence of incorporation of the one or more nucleotides and/or nucleotide analogues into the resulting DNA is identified, e.g., as the nucleotides and/or analogues are incorporated. The reaction mixture is optionally contained in, and the subjecting and identifying steps are optionally performed in, a zero mode waveguide.

The recombinant polymerase optionally also exhibits an increased residence time for a second (and optionally third, fourth, etc.) nucleotide analogue. The first and second (and third, fourth, etc.) nucleotide analogues can be included in the reaction mixture and incorporated into the resulting DNA. Typically, the first and second (and third, fourth, etc.) analogues comprise different labels which are distinguished from each other during the identifying step, so that the identity of each analogue can be conveniently identified as its incorporation is detected. The different labels are optionally different fluorophores.

A variety of DNA polymerases are optionally modified to have increased residence times. For example, the recombinant DNA polymerase is optionally homologous to a Φ29 polymerase, a Taq polymerase, an exonuclease deficient Taq polymerase, a DNA Pol I polymerase, a T7 polymerase, an RB69 polymerase, a T5 polymerase, or a polymerase corresponding to a Klenow fragment of a DNA Pol I polymerase. In one class of embodiments, the recombinant DNA polymerase is a modified recombinant Φ29-type DNA polymerase. The modified recombinant Φ29-type polymerase used in the methods can be any of those noted above with reference to the compositions, and the properties of the modified recombinant Φ29-type polymerase used in the methods can be any of those noted in reference to compositions. For example, the residence time of the modified recombinant polymerase for the first (and optional second, third, fourth, etc.) nucleotide analogue is typically greater than about 20 msec, and preferably between about 20 msec and about 300 msec when operating under typical template replication conditions. In one class of embodiments, the residence time of the modified recombinant polymerase for the nucleotide analogue is between about 55 msec and about 100 msec. Similarly, the nucleotide analogues used in the methods can be any of those noted in reference to the compositions herein. For example, the first (and/or optional second, third, fourth, etc.) nucleotide analogue can be a phosphate-labeled nucleotide analogue and/or a labeled nucleotide analogue having from 3-6 phosphate groups. As just one specific example, the nucleotides and/or analogues included in the reaction mixture can be A488dA4P, A633dC4P, A546dG4P or FAM-amb-A532dG4P, and A594dT4P or FAM-amb-A594dT4P or a similar set of differently labeled, phosphate labeled, tetraphosphate analogues.

In one aspect, the present invention includes methods of making the compositions herein. For example, in one aspect, a method of making a modified recombinant DNA polymerase (e.g., any of those discussed with respect to the compositions or methods herein, e.g., a modified recombinant Φ29-type DNA polymerase) is provided. For example, the methods can include structurally modeling a first DNA polymerase, e.g., using any available crystal structure and molecular modeling software or system. Based on the modeling, one or more amino acid residue positions in the polymerase are identified as targets for mutation. The first DNA polymerase is mutated at the one or more positions to introduce at least one intramolecular interaction predicted to stabilize the closed complex of the polymerase or to remove at least one intramolecular interaction predicted to destabilize the closed complex. Typically, the residence time of the recombinant mutant polymerase for one or more nucleotide analogues is then assayed to determine whether the resulting recombinant polymerase displays an increased residence time for a nucleotide analogue as compared to the first polymerase. Further, the residence time of the modified recombinant polymerase for a natural nucleotide can also be determined (e.g., where the polymerase desirably includes both analogue and natural nucleotide incorporation activity).

A library of recombinant DNA polymerases can be made and screened. For example, a plurality of members of the library can be made to include one or more mutations at the one or more positions, and then the library can be screened to identify at least one member exhibiting an increased residence time for the nucleotide analogue.

As an alternative or as an addition to the modified or engineered polymerases described above, the invention also provides nucleotides or nucleotide analogues that are selected, modified, or engineered to achieve similar goals as the polymerase enzymes described above, namely providing enhanced residence times to facilitate observation of incorporation events.

For example, at least one aspect of the invention relates to use of α-thiophosphate nucleotide analogues in sequencing applications, particularly α-thio-substituted triphosphate nucleotide analogues or α-thio-substituted nucleotide analogues having at least four phosphate groups. Thus, one general class of embodiments provides methods of sequencing a DNA template, in which a reaction mixture is provided that includes the DNA template, a replication initiating moiety that complexes with or is integral to the template, a DNA polymerase capable of replicating at least a portion of the template using the moiety in a template-dependent polymerization reaction, and one or more nucleotides and/or nucleotide analogues, which nucleotides and/or nucleotide analogues comprise at least a first α-thiophosphate nucleotide analogue having at least three (e.g., at least four) phosphate groups. The reaction mixture is subjected to a polymerization reaction in which the polymerase replicates at least a portion of the template in a template-dependent manner, whereby the one or more nucleotides and/or nucleotide analogues are incorporated into the resulting DNA. To determine the sequence of the template, a time sequence of incorporation of the one or more nucleotides and/or nucleotide analogues into the resulting DNA is identified, e.g., as the nucleotides and/or analogues are incorporated. The reaction mixture is optionally contained in, and the subjecting and identifying steps are optionally performed in, a zero mode waveguide.

As noted, at least a first α-thiophosphate nucleotide analogue having at least three (e.g., at least four) phosphate groups is provided in the reaction mixture. Optionally, at least two or at least three α-thiophosphate nucleotide analogues each having at least three (e.g., at least four) phosphate groups are provided in the reaction mixture. For example, in one class of embodiments, four α-thiophosphate nucleotide analogues, each having at least four phosphate groups, are provided in the reaction mixture (typically, the four analogues represent analogous compounds to the four natural nucleotides, A, T, G and C). In embodiments in which more than one analogue is provided and the analogues are labeled, the analogues preferably comprise different labels (e.g., different fluorophores) which are distinguished from each other during the identifying step, so that the identity of each analogue can be conveniently identified as its incorporation is detected.

Any of the variety of DNA polymerases known in the art and/or described herein can be used in the methods. For example, the DNA polymerase is optionally a Φ29-type DNA polymerase, a Taq polymerase, an exonuclease deficient Taq polymerase, a DNA Pol I polymerase, a T7 polymerase, an RB69 polymerase, a T5 polymerase, or a polymerase corresponding to a Klenow fragment of a DNA Pol I polymerase. The polymerase can, but need not, be a modified recombinant polymerase having an increased residence time, as described above.

The polymerase optionally includes one or more mutations relative to the wild-type polymerase that reduce or eliminate endogenous exonuclease activity. For example, relative to the wild-type Φ29 DNA polymerase, N62 is optionally mutated or deleted to reduce exonuclease activity; e.g., the polymerase can include an N62D mutation. As additional examples, the polymerase can include one or more of D12A, T15I, E14I, and D66A mutations. Similarly, the DNA polymerase optionally includes additional features exogenous or heterologous to a corresponding DNA polymerase such as a wild-type or nuclease deficient polymerase. For example, the polymerase can be a recombinant polymerase that includes one or more exogenous affinity tags, e.g., purification or substrate binding tags.

In one exemplary class of embodiments, the first (and optional second, third, fourth, etc.) nucleotide analogue is a phosphate-labeled nucleotide analogue. For example, the analogue can be labeled on the terminal phosphate. In other embodiments, the analogue is a base or sugar-labeled nucleotide analogue. Typically, the analogue has from four to six phosphate groups (e.g., the nucleotide analogue is a tetraphosphate, a pentaphosphate or a hexaphosphate). In one class of embodiments, the first (and optional second, third, fourth, etc.) nucleotide analogue is an α-thiotetraphosphate analogue, optionally labeled with a fluorophore on the delta phosphate. The analogue residue that is incorporated into a growing polynucleotide by the polymerase can be the same as a natural residue, e.g., where a label or other moiety of the analogue is removed by action of the polymerase during incorporation, or the analogue residue can have one or more feature that distinguishes it from a natural nucleotide residue.

Compositions including α-thiophosphate nucleotide analogues are also a feature of the invention. Thus, one class of embodiments provides a composition comprising a first α-thiophosphate nucleotide analogue having at least three (e.g., at least four) phosphate groups. The composition optionally includes at least two α-thiophosphate nucleotide analogues each having at least three (e.g., at least four) phosphate groups, e.g., three, four, or more such analogues. In embodiments in which more than one analogue is provided and the analogues are labeled, the analogues preferably comprise different labels (e.g., different fluorophores) which are distinguishable from each other.

As for the related methods above, the first (and optional second, third, fourth, etc.) nucleotide analogue can be a phosphate-labeled nucleotide analogue. For example, the analogue can be labeled on the terminal phosphate. In other embodiments, the analogue is a base or sugar-labeled nucleotide analogue. Typically, the analogue has from four to six phosphate groups (e.g., the nucleotide analogue is a tetraphosphate, a pentaphosphate or a hexaphosphate). In one class of embodiments, the first (and optional second, third, fourth, etc.) nucleotide analogue is an α-thiotetraphosphate analogue, optionally labeled with a fluorophore on the delta phosphate.

A DNA polymerase (e.g., any of those noted herein), a DNA template, a replication initiating moiety that complexes with the template or is integral to it, and/or a nascent or completed polynucleotide complementary to at least a portion of the template are optionally included in compositions of the invention, e.g., in which the polymerase incorporates the thiophosphate nucleotide analogue(s) into a copy nucleic acid in response to the template DNA. The template DNA can be amplified and/or sequenced. Thus, the composition can be present in a DNA amplification and/or sequencing system. Optionally, in one class of embodiments, the composition is present in a DNA sequencing system comprising a zero mode waveguide.

DEFINITIONS

Figure 1:
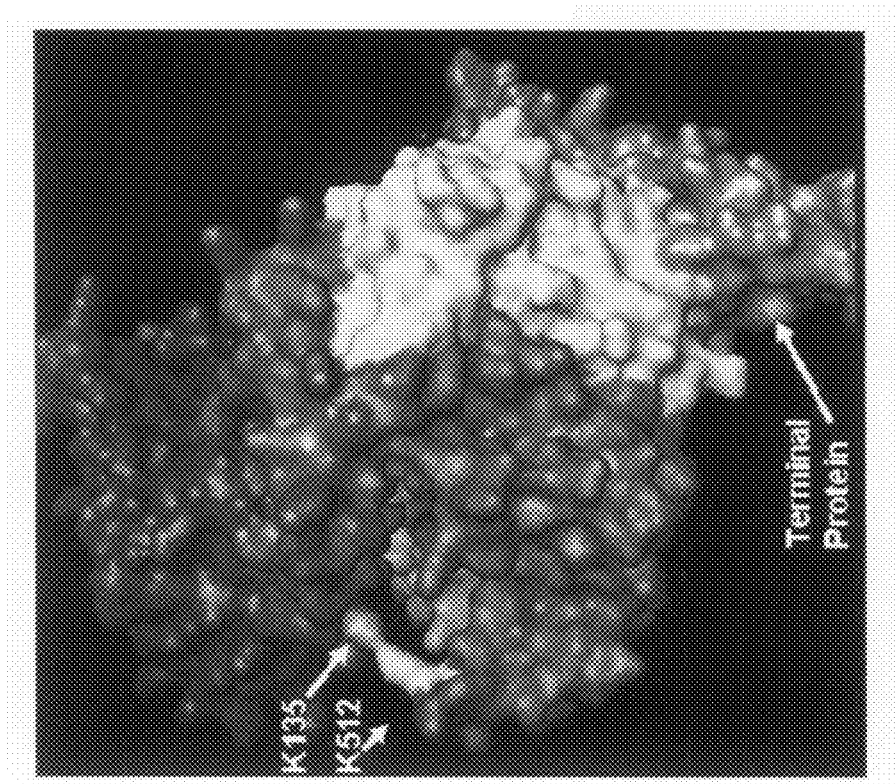
FIG. 1 illustrates the structure of the Φ29 polymerase (left) and of the Φ29 polymerase bound to terminal protein (right). Positions of residues K135 and K512 are indicated by arrows.
Figure 1:
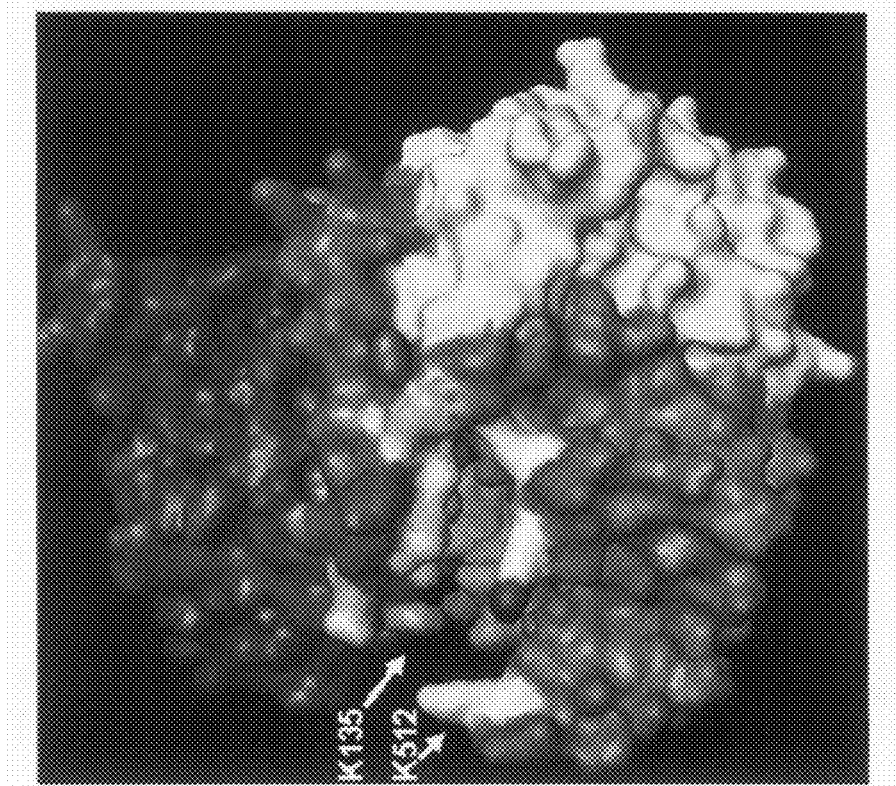

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by +/−10% of the value, or optionally +/−5% of the value, or in some embodiments, by +/−1% of the value so described.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer. Correspondence of positions is typically determined by aligning the relevant amino acid or polynucleotide sequences.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ29 DNA polymerase; examples include the B103, GA-1, PZA, Φ15, BS32, M2Y, Nf, G1, Cp-1, PRD1, PZE, SF5, Cp-5, Cp-7, PR4, PR5, PR722, and L17 DNA polymerases. A modified recombinant Φ29-type DNA polymerase includes one or more mutations relative to naturally-occurring wild-type Φ29-type DNA polymerases, for example, one or more mutations that increase residence time for a nucleotide analogue relative to a corresponding wild-type polymerase, and may include additional alterations or modifications over wild-type Φ29-type DNA polymerases, such as deletions, insertions, and/or fusions of additional peptide or protein sequences (e.g., for immobilizing the polymerase on a surface or otherwise tagging the polymerase enzyme).

A variety of additional terms are defined or otherwise characterized herein.

DETAILED DESCRIPTION

Overview

A variety of technologies rely on the incorporation of labels into nucleic acids to observe the results of an experiment. For example, the outcome of sequencing, nucleic acid amplification, and nick translation reactions are all typically monitored by labeling product nucleic acids. This is often done by covalently or non-covalently binding labels to the product nucleic acids, e.g., by binding labeled probes to the product nucleic acid. In other approaches, nucleotide analogues are incorporated into product nucleic acids during synthesis of the product nucleic acid. This typically occurs, e.g., in sequencing by incorporation methods, and in certain real-time PCR (RT-PCR) and real-time LCR reactions (RT-LCR). A label present on the analogue can be incorporated into the DNA, or it can be released by action of the polymerase. Incorporation or release of the label can be monitored to monitor incorporation of an analogue residue into the product nucleic acid.

The invention is generally directed to modified or engineered compositions that are characterized by increased retention times for polymerase-nucleotide interactions during template dependent incorporation of nucleotides. In particular, the invention provides, e.g., compositions including one or more of engineered or modified polymerase enzymes and/or engineered or modified nucleotides or nucleotide analogues, where the composition exhibits an increased time of retention of the nucleotide or analogue by the polymerase when the nucleotide or nucleotide analogue is incorporated by the polymerase enzyme during template dependent polymerase mediated nucleic acid synthesis.

Accordingly, among other aspects, the present invention provides new polymerases that incorporate nucleotide analogues, such as dye labeled phosphate labeled analogues, into a growing template copy during DNA amplification. These polymerases are modified such that they have increased residence times for one or more nucleotide analogues as compared to the corresponding wild-type polymerases (e.g., polymerases from which modified recombinant polymerases of the invention were derived, e.g., by mutation).

These new polymerases are particularly well suited to DNA amplification and/or sequencing applications, particularly sequencing protocols that include detection in real time of incorporation of labeled analogues into DNA amplicons, since the increased residence times facilitate discrimination of nucleotide incorporation events from non-incorporation events such as transient binding of a mis-matched nucleotide. Another aspect of the invention relates to use of α-thiophosphate nucleotide analogues having at least four phosphate groups in sequencing applications. Without being bound to a particular theory of operation, it is believed that the α-thio substitution in the analogues slows incorporation of the nucleotides, again facilitating discrimination of nucleotide incorporation events from non-incorporation events in sequencing applications or other techniques in which incorporation is detected in real time.

DNA Polymerases

DNA polymerases that can be modified to have increased residence times for nucleotide analogues are generally available. DNA polymerases have relatively recently been classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29 is available.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. Any of these available polymerases can be modified in accordance with the invention to increase residence times for nucleotide analogues. Many such polymerases that are suitable for modification are available, e.g., for use in sequencing, labeling and amplification technologies. For example, Human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to increase residence times for nucleotide analogues include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified to have an increased residence time is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Similarly, the modified recombinant DNA polymerase can be homologous to another Φ29-type DNA polymerase, such as B103, GA-1, PZA, Φ15, BS32, M2Y, Nf, G1, Cp-1, PRD1, PZE, SF5, Cp-5, Cp-7, PR4, PR5, PR722, L17, Φ21, or like polymerases. For nomenclature, see also, Meijer et al. (2001) "Φ29 Family of Phages" Microbiology and Molecular Biology Reviews, 65(2):261-287.

Nucleotide Analogues

As discussed, various polymerases of the invention can incorporate one or more nucleotide analogues into a growing oligonucleotide chain. Upon incorporation, the analogue can leave a residue that is the same as or different than a natural nucleotide in the growing oligonucleotide (the polymerase can incorporate any non-standard moiety of the analogue, or can cleave it off during incorporation into the oligonucleotide). A "nucleotide analogue" herein is a compound, that, in a particular application, functions in a manner similar or analogous to a naturally occurring nucleoside triphosphate (a "nucleotide"), and does not otherwise denote any particular structure. A nucleotide analogue is an analogue other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

Many nucleotide analogues are available. These include analogue structures with core similarity to naturally occurring nucleotides, such as those that comprise one or more substituent on a phosphate, sugar or base moiety of the nucleoside or nucleotide relative to a naturally occurring nucleoside or nucleotide. In one embodiment, the nucleotide analogue includes three phosphate containing groups; for example, the analogue can be a labeled nucleoside triphosphate analogue and/or an α-thiophosphate nucleotide analogue having three phosphate groups. In one embodiment, a nucleotide analogue can include one or more extra phosphate containing groups, relative to a nucleoside triphosphate. For example, a variety of nucleotide analogues that comprise, e.g., from 4-6 phosphates are described in detail in U.S. patent application Ser. No. 11/241,809, filed Sep. 29, 2005, and incorporated herein by reference in its entirety for all purposes. Other exemplary useful analogues, including tetraphosphate and pentaphosphate analogues, are described in U.S. Pat. No. 7,041,812, incorporated herein by reference in its entirety for all purposes.

For example, the analogue can include a labeled compound of the formula:

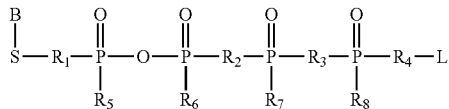

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, C(OH)CH$_2$R where R is 4-pyridine or 1-imidazole, provided that $R_4$ may additionally be selected from

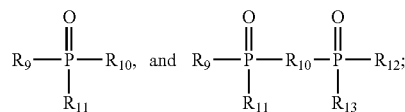

$R_5$, $R_6$, $R_7$, $R_8$, $R_{11}$ and $R_{13}$ are, when present, each independently selected from 0, BH$_3$, and S; and $R_9$, $R_{10}$ and $R_{12}$ are independently selected from O, NH, S, methylene, substituted methylene, CNH$_2$, CH$_2$CH$_2$, C(OH)CH$_2$R where R is 4-pyridine or 1-imidazole. In some cases, phosphonate analogues may be employed as the analogues, e.g., where one of $R_2$, $R_3$, $R_4$, $R_9$, $R_{10}$ or $R_{12}$ are not O, e.g., they are methyl etc. See, e.g., U.S. patent application Ser. No. 11/241,809, previously incorporated herein by reference in its entirety for all purposes.

The base moiety incorporated into the analogue is generally selected from any of the natural or non-natural nucleobases or nucleobase analogues, including, e.g., purine or pyrimidine bases that are routinely found in nucleic acids and available nucleic acid analogues, including adenine, thymine, guanine, cytidine, uracil, and in some cases, inosine. As noted, the base optionally includes a label moiety. For convenience, nucleotides and nucleotide analogues are generally referred to based upon their relative analogy to naturally occurring nucleotides. As such, an analogue that operates, functionally, like adenosine triphosphate, may be generally referred to herein by the shorthand letter A. Likewise, the standard abbreviations of T, G, C, U and I, may be used in referring to analogues of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogues, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogues, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogues, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$) group. The labeling groups employed in the analogues of the invention may comprise any of a variety of detectable labels. Detectable labels generally denote a chemical moiety that provides a basis for detection of the analogue compound separate and apart from the same compound lacking such a labeling group. Examples of labels include, e.g., optical labels, e.g., labels that impart a detectable optical property to the analogue, electrochemical labels, e.g., labels that impart a detectable electrical or electrochemical property to the analogue, and physical labels, e.g., labels that impart a different physical or spatial property to the analogue, e.g., a mass tag or molecular volume tag. In some cases individual labels or combinations may be used that impart more than one of the aforementioned properties to the analogues of the invention.

Optionally, the labeling groups incorporated into the analogues comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogues. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogues incorporated by the polymerases of the present invention, are described in, e.g., U.S. Patent Application Publication No. 2003/0124576, previously incorporated herein by reference in its entirety for all purposes.

Additional details regarding analogues and methods of making such analogues can be found in U.S. patent application Ser. No. 11/241,809, filed Sep. 29, 2005, and incorporated herein by reference in its entirety for all purposes.

Thus, in one illustrative example, the analogue can be a phosphate analogue (e.g., an analogue that has more than the typical number of phosphates found in nucleoside triphosphates) that include, e.g., an Alexa dye label. For example, an Alexa488 dye can be labeled on a delta phosphate of a tetraphosphate analogue (denoted, e.g., A488dC4P or A488dA4P, for the Alexa488 labeled tetraphosphate analogues of C and A, respectively), or an Alexa568 or Alexa633 dye can be used (e.g., A568dC4P and A633dC4P, respectively, for labeled tetraphosphate analogues of C), or an Alexa546 dye can be used (e.g., A546dG4P), or an Alexa594 dye can be used (e.g., A594dT4P). Similarly, to facilitate color separation, a pair of fluorophores exhibiting FRET (fluorescence resonance energy transfer) can be labeled on a delta phosphate of a tetraphosphate analogue (denoted, e.g., FAM-amb-A532dG4P or FAM-amb-A594dT4P).

Applications for Enhanced Nucleic Acid Amplification and Sequencing

Polymerases of the invention, e.g., modified recombinant polymerases, natural nucleotides and/or nucleotide analogues, and nucleic acid templates (DNA or RNA) are optionally used to copy the template nucleic acid. That is, a mixture of the polymerase, nucleotide analogues, and optionally natural nucleotides and other reagents, the template and a replication initiating moiety is reacted such that the polymerase synthesizes nucleic acid (e.g., extends the primer) in a template-dependent manner. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as a initiating moiety. At least one nucleotide analogue can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

Incorporation of labeled nucleotide analogues by the polymerases of the invention is particularly useful in a variety of different nucleic acid analyses, including real-time monitoring of DNA polymerization. The label can itself be incorporated, or more preferably, can be released during incorporation of the analogue. For example, analogue incorporation can be monitored in real-time by monitoring label release during incorporation of the analogue by the polymerase. The portion of the analogue that is incorporated can be the same as a natural nucleotide, or can include features of the analogue that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analogue, e.g., in a solid phase assay, or can arise upon the incorporation reaction. For example, in the case of FRET labels where a bound label is quenched and a free label is not, release of a label group from the incorporated analogue can give rise to a fluorescent signal. Alternatively, the enzyme may be labeled with one member of a FRET pair proximal to the active site, and incorporation of an analogue bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analogue that is readily distinguishable from non-incorporated nucleotide analogues. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781, and U.S. Pat. No. 6,917,726, each of which is incorporated herein by reference in its entirety for all purposes. See also Levene et al. (2003) "Zero-mode waveguides for single-molecule analysis at high concentrations" Science 299:682-686 and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogues. For example, in certain embodiments, labeled analogues are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analogue that is complementary to such nucleotide, and incorporates that analogue into the nascent and growing nucleic acid strand. In one aspect, incorporation can result in a label being released, e.g., in polyphosphate analogues, cleaving between the $\alpha$ and $\beta$ phosphorus atoms in the analogue, and consequently releasing the labeling group (or a portion thereof). The incorporation event is detected, either by virtue of a longer presence of the analogue and, thus, the label, in the complex, or by virtue of release of the label group into the surrounding medium. Where different labeling groups are used for each of the types of analogues, e.g., A, T, G or C, identification of a label of an incorporated analogue allows identification of that analogue and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide.

In addition to their use in sequencing, the analogues and polymerases of the invention are also useful in a variety of other genotyping analyses, e.g., SNP genotyping using single base extension methods, real time monitoring of amplification, e.g., RT-PCR methods, and the like. Further details regarding sequencing and nucleic acid amplification can be found, e.g., in Sambrook, Ausubel, and Innis, all infra.

Enhanced Sequencing Using Modified Recombinant Polymerases with Increased Residence Times As noted above, nucleic acid sequencing can be performed by monitoring the polymerization reaction in real time, e.g., using a zero mode waveguide, such that the sequential incorporation of nucleotides and/or nucleotide analogues is detected. Also as noted above, incorporation of the labeled nucleotide analogue into the nascent and growing nucleic acid strand can be detected by virtue of a longer presence of the analogue, and thus the label, in the complex with polymerase as a result of incorporation (e.g., prior to release of or photo-bleaching of the label). This longer signal event provides a basis for distinguishing between incorporated bases and bases that transiently diffuse into and out of the observation region, or that are otherwise not incorporated into the nascent strand. While effective, it would be nonetheless desirable to enhance the distinction between incorporated and unincorporated bases by providing a further enhanced residence time, and thus, detectable signal duration, associated with incorporation. For example, the residence time of certain phosphate labeled nucleotide analogues during incorporation can be shorter than may be desired (for example, approximately 20-40 msec) relative to other signal producing events which may occur on time scales that result in signals of duration of a similar order to incorporation events, but that do not represent incorporation of an analogue into the growing nucleic acid strand, potentially leading to sequencing errors. Examples include sampling (binding and release of a mismatched nucleotide or analogue) and branching (binding of the appropriate nucleotide or analogue but without its incorporation).

Use of a modified recombinant polymerase having an increased residence time for the nucleotide analogue is thus advantageous, since it preferably extends the duration of only the signal that represents incorporation of an appropriate, correctly matched nucleotide analogue.

Enhanced Sequencing Using Modified Analogues

Use of modified nucleotide analogues is similarly advantageous. In particular, by providing a modified nucleotide analogue that resides for a longer duration within the polymerase template complex during incorporation, one can increase the length of the signal duration associated with that incorporation, providing further distinction between actual incorporation and other transient events. For example, in the case of the preferred aspects of the invention, the $\alpha$-thio substitution in an $\alpha$-thiophosphate analogue is thought to affect (slow) the forward and backward rates of the bond formation steps, while all other rate constants for incorporation of the phosphorothioate nucleotide analogue remain unchanged (see Benkovic and Schray (1973) in *The Enzymes*, Boyer (ed) pp 201-238, Academic Press, New York; Eger and Benkovic (1992) Biochemistry 31:9227-9236; and Mizrahi et al. (1985) Biochemistry 24:4010-4018). The $\alpha$-thio substitution thus increases the duration of signals representing incorporation of the analogue, facilitating their discrimination from spurious signals arising from events such as branching, sampling, or nonspecific binding of the analogue to the polymerase.

Modifying DNA Polymerases to Increase Residence Times

Structure-Based Design of Modified Recombinant Polymerases

Structural data for a polymerase can be used to conveniently identify amino acid residues as candidates for mutagenesis to create modified recombinant polymerases having increased residence times for nucleotide analogues. For example, analysis of the three-dimensional structure of a polymerase can identify residues that can be mutated to create a salt bridge or introduce hydrophobic or other interactions that stabilize the closed complex of the polymerase bound to a DNA template and an incoming nucleotide or nucleotide analogue and that therefore increase residence time. Such mutations can add or alter charge, hydrophobicity, size, or the like.

The three-dimensional structures of a large number of DNA polymerases have been determined by x-ray crystallography and nuclear magnetic resonance (NMR) spectroscopy, including the structures of polymerases with bound templates, nucleotides, and/or nucleotide analogues. Many such structures are freely available for download from the Protein Data Bank, at www(dot)rcsb(dot)org/pdb. Structures, along with domain and homology information, are also freely available for search and download from the National Center for Biotechnology Information's Molecular Modeling Data- Base, at www(dot)ncbi(dot)nlm(dot)nih(dot)gov/Structure/ MMDB/mmdb(dot)shtml. The structures of additional polymerases can be modeled, for example, based on homology of the polymerases with polymerases whose structures have already been determined. Alternatively, the structure of a given polymerase, optionally complexed with a nucleotide analogue, or the like, can be determined.

Techniques for crystal structure determination are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide*, 2nd Edition Wiley Publishers, New York; Ladd and Palmer (1993) *Structure determination by X-ray crystallography*. 3rd Edition Plenum Press, New York; Blundell and Johnson (1976) *Protein Crystallography* Academic Press, New York; Glusker and Trueblood (1985) *Crystal structure analysis: A primer*, 2nd Ed. Oxford University Press, New York; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) *Chapter* 15 of *Crystallographic Computing*, Volume 5 IUCr/Oxford University Press; Murthy (1996) *Chapter* 5 of *Crystallographic Methods and Protocols* Humana Press; Dauter et al. (2000) "Novel approach to phasing proteins: derivatization by short cryosoaking with halides" Acta Cryst. D56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl. Acad. Sci. USA, 88:4240-4244; and Gavira et al. (2002) "Ab initio crystallographic structure determination of insulin from protein to electron density without crystal handling" Acta Cryst. D58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276: 307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and O (Jones et al. (1991) "Improved methods for building protein models in electron density maps and the location of errors in these models" Acta Crystallogr A 47 (Pt 2):110-119).

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis*, 2nd Edition, Wiley-VCH; Macomber (1998) *A Complete Introduction to Modern NMR Spectroscopy*, Wiley-Interscience; Downing (2004) *Protein NMR Techniques* (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curr. Opin. Struct. Biol. 4:738; Pervushin et al. (1997) Proc. Natl. Acad. Sci. U.S.A. 94:12366; Fiaux et al. (2002) Nature 418: 207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

If desired, the structure of a polymerase with a given nucleotide analogue incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site region of the polymerase can be identified, for example, by homology with other polymerases, examination of polymerase-template or polymerase-nucleotide co-complexes, biochemical analysis of mutant polymerases, and/or the like. The position of a nucleotide analogue in the active site can be modeled, for example, based on the previously determined location of another nucleotide or nucleotide analogue in the active site.

Such modeling of the nucleotide analogue in the active site can involve simple visual inspection of a model of the polymerase, for example, using molecular graphics software such as the PyMOL viewer (open source, freely available on the World Wide Web at www(dot)pymol(dot)org) or Insight II (commercially available from Accelrys at (www(dot)accelrys(dot)com/products/insight). Alternatively, modeling of the nucleotide analogue in the active site of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at www(dot)usm(dot)maine(dot)edu/~rhodes/SPVTut/index (dot)html; and Methods for Protein Simulations and Drug Design at www(dot)dddc(dot)ac(dot)cn/embo04; and references therein. Software to facilitate such modeling is widely available, for example, the CHARMm simulation package, available academically from Harvard University or commercially from Accelrys (at www(dot)ccelrys(dot)com), the Discover simulation package (included in Insight II, supra), and Dynama (available at www(dot)cs(dot)gsu(dot)edu/~cscrwh/progs/progs(dot)html). See also an extensive list of modeling software at www(dot)netsci(dot)org/Resources/Software/Modeling/MMMD/top(dot)html.

Visual inspection and/or computational analysis of a polymerase model, including comparison of models of the polymerase in different states, can identify relevant features of the polymerase, including, for example, residues that can be mutated to stabilize the closed complex of the polymerase, e.g., relative to the open complex. For example, one or more residues that are in closer proximity to each other in the closed complex than the open complex can be replaced with residues having complementary features, for example, oppositely charged residues (e.g., aspartic or glutamic acid, and lysine, arginine, or histidine), residues that can hydrogen bond with each other (e.g., serine, threonine, histidine, asparagine, or glutamine), hydrophobic residues that can interact with each other, aromatic residues that can engage in π-π or edge-face stacking interactions, residues that can engage in cation-π interactions, or the like.

Figure 2:
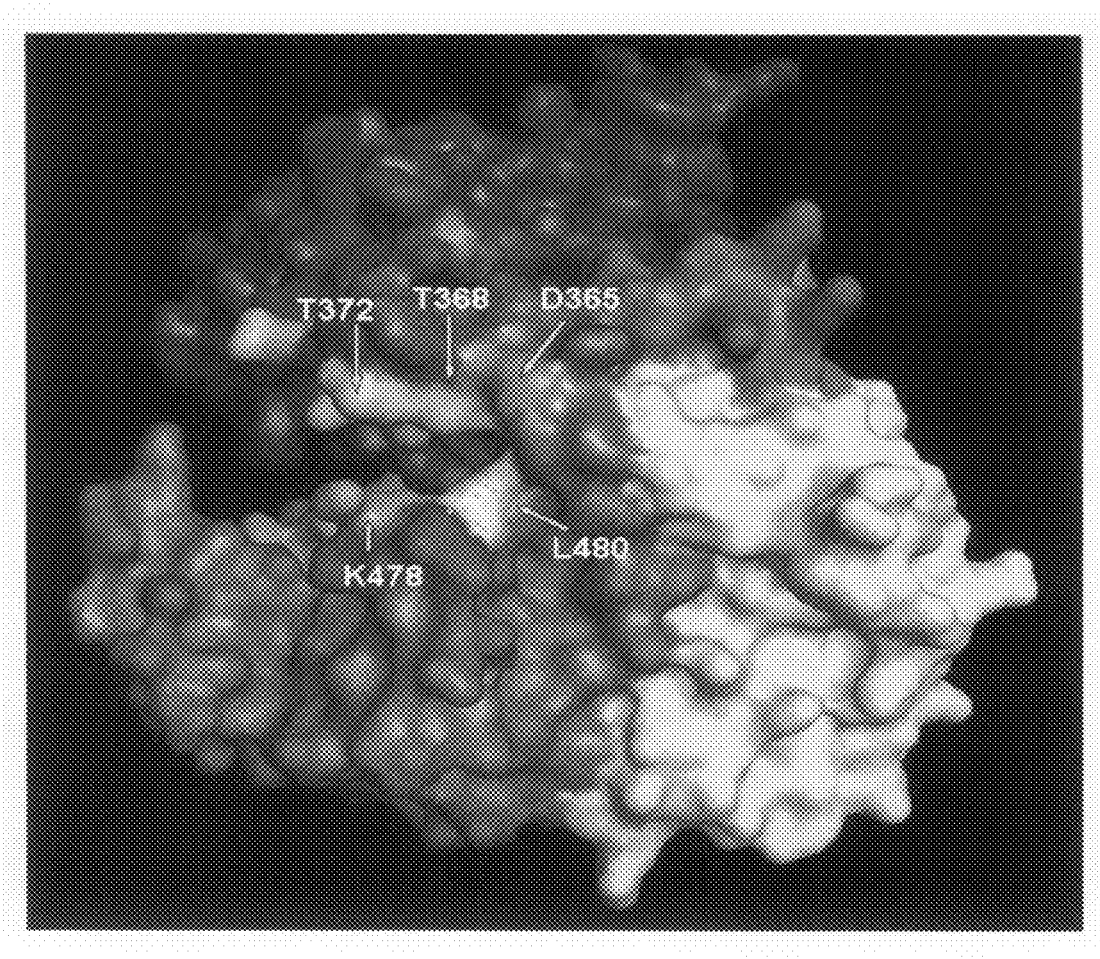
FIG. 2 illustrates the structure of Φ29; positions of residues D365, T368, T372, K478, and L480 are indicated by arrows.
Figure 3:
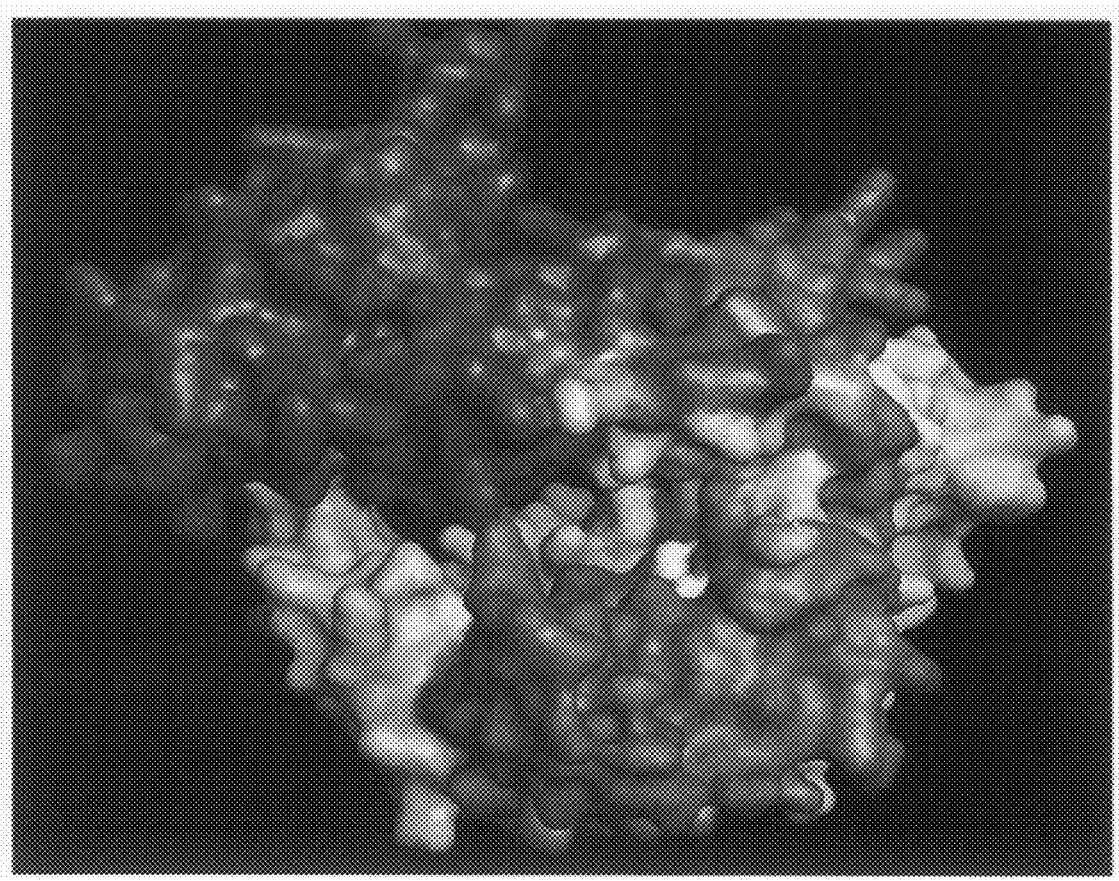
FIG. 3 illustrates the structure of Φ29, from a different angle than is shown in FIG. 2.
Figure 4:
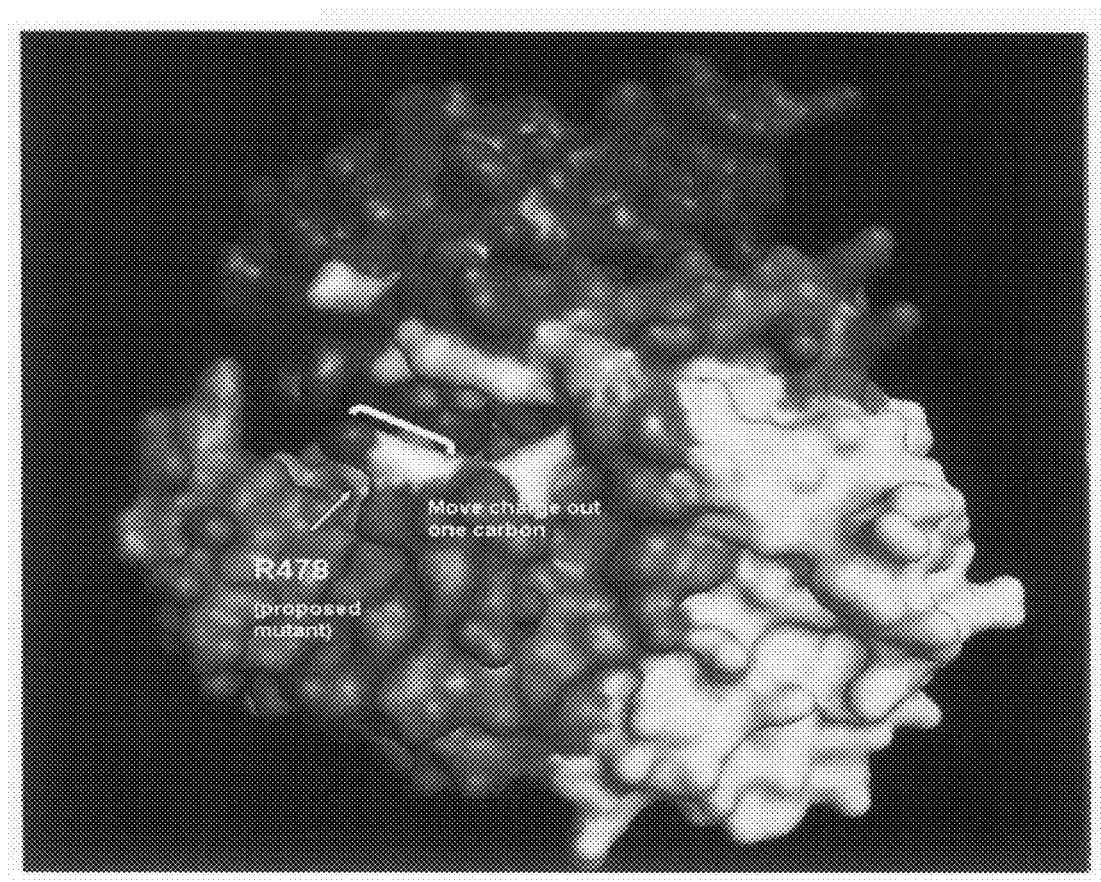
FIG. 4 illustrates the structure of a K478R mutant.

As just one specific example of such structure-based design, comparison of a model of the Φ29 polymerase (FIG. 1, left; see Kamtekar et al. (2004) "Insights into strand displacement and processivity from the crystal structure of the protein-primed DNA polymerase of bacteriophage Φ29" Mol. Cell. 16(4): 609-618) with a model of the Φ29 polymerase complex with terminal protein (FIG. 1, right; see Kamtekar et al. (2006) "The phi29 DNA polymerase:protein-primer structure suggests a model for the initiation to elongation transition" EMBO J. 25(6):1335-43) revealed some structural changes in Φ29. Although the terminal protein complex does not truly represent the closed complex of Φ29 polymerase, the observed changes nevertheless are indicative of partial rearrangements within Φ29 as it forms the closed complex. One major difference observed upon inspection of the two structures was the close proximity of K135 and K512 upon binding of terminal protein (FIG. 1). Without limitation to any particular mechanism, mutations reversing the charge of one of these two residues can thus introduce a salt bridge that stabilizes the closed conformation; examples include K135D (i.e., mutation of Lys 135 to Asp) or K135E mutations, which introduce residues that can interact with K512, and K512D or K512E, which introduce residues that can interact with K135. Other exemplary mutations that can be introduced into the Φ29 polymerase to introduce a salt bridge to stabilize the closed complex include, e.g., L480K or L480R, to introduce a residue that can interact with D365; a combination of either T368D or T368E and L480K mutations; T372D or T372E, to introduce a residue that can interact with K478 or K478R (illustrated in FIG. 4); or a combination of either T372R or T372K with either K478D or K478E. The positions of these residues are indicated in FIG. 2; another view of Φ29 is shown in FIG. 3. Similarly, these (or other) residues can be mutated to introduce hydrophobic interactions, hydrogen bonds, or other interactions that stabilize the closed conformation. Table 1 presents approximate distances between pairs of residues in the open complex which, without limitation to any particular mechanism, are likely from visual inspection of the model of Φ29 to be in closer proximity in the closed complex. It will be evident that catalytic and/or highly conserved residues are less preferred targets for mutation.

TABLE 1

Open complex distances.

| Residue 1 | Residue 2 | Distance |
|---|---|---|
| T368 | K478 | ≈12.08 Å |
| T368 | LA80* | ≈6.08 Å |
| D365 | L480* | ≈6.90 Å |
| T372 | K478 | ≈8.16 Å |

*L480 is close to Y259 and there may be some van der Waals interactions

Thus, in addition to methods of using the polymerases and other compositions herein, the present invention also includes methods of making the polymerases. As described, methods of making a modified recombinant DNA polymerase can include structurally modeling a first polymerase, e.g., using any available crystal structure and molecular modeling software or system. Based on the modeling, one or more amino acid residue positions in the polymerase are identified as targets for mutation. The first DNA polymerase is mutated at the one or more positions to introduce at least one intramolecular interaction predicted to stabilize the closed complex of the polymerase or to remove at least one intramolecular interaction predicted to destabilize the closed complex. Typically, the residence time of the modified recombinant mutant polymerase for one or more nucleotide analogues is then assayed to determine whether the resulting modified recombinant polymerase displays an increased residence time for a nucleotide analogue as compared to the first polymerase.

Mutating Active Site Regions

Various types of mutagenesis are optionally used in the present invention, e.g., to modify polymerases to produce variants having increased residence times, e.g., in accordance with polymerase models and model predictions as discussed above. In general, any available mutagenesis procedure can be used for making such mutants. Such mutagenesis procedures optionally include selection of mutant nucleic acids and polypeptides for one or more activity of interest (e.g., increased residence time for a nucleotide analogue). Procedures that can be used include, but are not limited to: site-directed point mutagenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill.

Optionally, mutagenesis can be guided by known information from a naturally occurring polymerase molecule, or of a known altered or mutated polymerase (e.g., using an existing mutant polymerase that displays reduced exonuclease activity), e.g., sequence, sequence comparisons, physical properties, crystal structure and/or the like as discussed above. However, in another class of embodiments, modification can be essentially random (e.g., as in classical DNA shuffling).

Additional information on mutation formats is found in: Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel")) and *PCR Protocols A Guide to Methods and Applications* (Innis et al. eds) Academic Press Inc. San Diego, Calif. (1990) (Innis). The following publications and references cited within provide still additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundström et al., Oligonucleotide-directed mutagenesis by microscale 'shot-gun' gene synthesis, Nucl. Acids Res. 13: 3305-3316 (1985); Kunkel, The efficiency of oligonucleotide directed mutagenesis, in *Nucleic Acids & Molecular Biology* (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181 (1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301 (1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91 (1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, *Methods in Enzymol.* 100:468-500 (1983); and Zoller & Smith, Oligonucleotide-directed mutagenesis: a simple method using two oligonucleotide primers and a single-stranded DNA template, *Methods in Enzymol.* 154:329-350 (1987). Additional details on many of the above methods can be found in *Methods in Enzymology* Volume 154, which also describes useful controls for trouble-shooting problems with various mutagenesis methods.

Determining Kinetic Parameters

The polymerases of the invention can be screened or otherwise tested to determine whether the polymerase displays a modified activity for or with a nucleotide analogue as compared to the first DNA polymerase (e.g., a corresponding wild-type polymerase from which the modified recombinant polymerase was derived). For example, residence time, $k_{cat}$, $K_m$, $V_{max}$, $k_{cat}/K_m$, $V_{max}/K_m$, $K_d$, and/or $k_{pol}$ of the modified recombinant DNA polymerase for the nucleotide analogue can be determined. Further, residence time, $k_{cat}$, $K_m$, $V_{max}$, $V_{max}/K_m$, $k_{cat}/K_m$, $K_d$, and/or $k_{pol}$ of the modified recombinant DNA polymerase for a natural nucleotide can also be determined (e.g., where the polymerase desirably includes both analogue and natural nucleotide incorporation activity).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher Km represents a complex with weaker binding. The ratio $k_{cat}/K_m$, sometimes called the specificity constant, represents the apparent rate constant for combination of substrate with free enzyme. The larger the specificity constant, the more efficient the enzyme is in binding the substrate and converting it to product.

The $k_{cat}$ (also called the turnover number of the enzyme) can be determined if the total enzyme concentration ([$E_T$], i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$.

Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

In one embodiment, using presteady-state kinetics, the nucleotide concentration dependence of the rate $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the burst equation; Product=$A[1-\exp(-k_{obs}*t)]+k_{ss}*t$ where A represents amplitude an estimate of the concentration of the enzyme active sites, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}*[S])*(K_m+[S])-1$ where [S] is the substrate concentration. The residence time is approximated by calculating $1/k_{pol}$. The residence time (the time the nucleotide or nucleotide analogue (or, in embodiments in which residence time is determined using terminal phosphate labeled analogues, technically the time the fluorescent dye attached to the terminal phosphate of the analogue) occupies the active site of the polymerase) can be approximated by measuring a rate limiting step in the polymerase kinetic pathway. The rate limiting step can be approximated using a rapid-quench experiment (also called a quench-flow measurement), for example, based on the methods described in Johnson (1986) "Rapid kinetic analysis of mechanochemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

A specific example of determination of residence times for nucleotide analogues using a quench flow measurement is presented in the Examples section below.

For a more thorough discussion of enzyme kinetics, see, e.g., Berg, Tymoczko, and Stryer (2002) *Biochemistry, Fifth Edition*, W. H. Freeman; Creighton (1984) *Proteins: Structures and Molecular Principles*, W. H. Freeman; and Fersht (1985) *Enzyme Structure and Mechanism, Second Edition*, W. H. Freeman.

In one aspect, the improved activity of the enzymes of the invention is measured with reference to a model analogue or analogue set and compared with a given parental enzyme. For example, in the case of enzymes derived from a Φ29 parental enzyme, an improved enzyme of the invention would have a greater residence time than the parental enzyme, e.g., wild type Φ29 or N62D Φ29, toward a given analogue. While the foregoing may be used as a characterization tool, it in no way is intended as a specifically limiting reaction of the invention.

Screening Polymerases

Screening or other protocols can be used to determine whether a polymerase displays a modified activity for a nucleotide analogue as compared to the first DNA polymerase. For example, residence time, $k_{cat}$, $K_m$, $V_{max}$, $k_{cat}/K_m$, $V_{max}/K_m$, $K_d$, or $k_{pol}$ of the modified recombinant DNA polymerase for the nucleotide analogue can be determined as discussed above. Further, residence time, $k_{cat}$, $K_m$, $V_{max}$, $k_{cat}/K_m$, $V_{max}/K_m$, $K_d$, or $k_{pol}$ of the modified recombinant DNA polymerase for a natural nucleotide can also be similarly determined (e.g., where the polymerase desirably includes both analogue and natural nucleotide incorporation activity).

In one desirable aspect, a library of modified recombinant DNA polymerases can be made and screened for these properties. For example, a plurality of members of the library can be made to include one or more mutations putatively affecting stability of the closed complex and/or randomly generated mutations (e.g., with different members including different mutations or different combinations of mutations), and the library can then be screened for the properties of interest. In general, the library can be screened to identify at least one member comprising a modified activity of interest (e.g., increased residence time).

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region) can be produced. Similarly, polymerase or polymerase domain libraries can be produced by yeast display or other similar display techniques. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.)).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. Furthermore, the patent and technical literature includes many examples of microfluidic systems which can interface directly with microwell plates for fluid handling.

Desirable Properties

The polymerases of the invention can include any of a variety of modified properties towards natural nucleotides and/or nucleotide analogues, depending on the application. Preferably, the modified recombinant polymerase of the invention is selected to have an increased residence time relative to a corresponding homologous wild-type polymerase with respect to a given nucleotide analogue. For example, the residence time of the modified recombinant polymerase for the nucleotide analogue is optionally between about 1.2 and about 5 times the residence time of the corresponding wild-type polymerase for the nucleotide analogue, typically at least about 1.5 times, e.g., between about 1.5 and about 4 times, between about 1.5 and about 3 times, or between about 1.5 and about 2.5 times. Preferred modified recombinant polymerases generally exhibit residence times for the nucleotide analogue of greater than about 20 msec (millisecond), for example, between about 20 msec and about 300 msec; particularly preferred polymerases exhibit residence times between about 55 msec and about 100 msec.

Preferably, the modified recombinant polymerase exhibits the increased residence time without compromising other steps in the catalytic cycle. For example, the recombinant polymerase preferably does not exhibit a decrease in processivity or fidelity or an increase in a branching fraction (the fraction of the nucleotides that after binding to the polymerase catalytic center dissociates rather than being incorporated to the extending DNA primer). As a similar example, the recombinant polymerase preferably does not exhibit an increased $K_m$ (and optionally even exhibits a decreased $K_m$).

Additional Example Details

A number of specific examples of modified polymerases are described herein, including examples of mutations expected to stabilize the closed conformation of the recombinant polymerase. For example, exemplary modified recombinant polymerases comprise one or more amino acid substitutions at one or more positions selected from the group consisting of position 135, position 368, position 372, position 478, position 480, and position 512, where numbering of positions is relative to wild-type Φ29 polymerase. For example, the modified recombinant polymerase can include one or more amino acid substitutions selected from the group consisting of K135D, K135E, T368D, T368E, T372D, T372E, T372R, T372K, K478D, K478E, K478R, L480K, L480R, K512D, and K512E. As a few specific examples, modified recombinant Φ29 type polymerases (e.g., Φ29 polymerases) of the invention can comprise at least one amino acid substitution or combination of substitutions selected from the group consisting of K135D, K135E, K512D, K512E, T372D, T372E, L480K, L480R, T368D and L480K, T368E and L480K, T372D and K478R, T372E and K478R, T372R and K478D, T372R and K478E, T372K and K478D, and T372K and K478E; for example, a modified recombinant Φ29 polymerase of the invention optionally includes at least one of these substitutions or combinations of substitutions in the amino acid sequence of SEQ ID NO:1, in a conservative variation of SEQ ID NO:1, or in an amino acid sequence comprising a sequence substantially identical to that of SEQ ID NO:1.

The modified recombinant polymerase optionally further includes one or more mutations/deletions relative to the wild-type polymerase that reduce or eliminate endogenous exonuclease activity. For example, relative to the wild-type Φ29 DNA polymerase, N62 is optionally mutated or deleted to reduce exonuclease activity; e.g., the polymerase can include an N62D mutation (see, e.g., SEQ ID NO:2 of U.S. patent application Ser. No. 11/645,223 "Polymerases for nucleotide analogue incorporation" by Hanzel et al. filed Dec. 21, 2006, incorporated herein by reference in its entirety for all purposes), D12A mutation, T15I mutation, E14I mutation, and/or D66A mutation. Similarly, the modified recombinant polymerase optionally further includes one or more mutations relative to the wild-type polymerase that improve incorporation of nucleotide analogues, for example, a deletion of residues 505-525, a deletion within residues 505-525, a K135A mutation, an E375H mutation, an E375S mutation, an E375K mutation, an E375R mutation, an E375A mutation, an E375Q mutation, an E375W mutation, an E375Y mutation, an E486A mutation, an E486D mutation, a K512A mutation, or a combination thereof, wherein numbering of positions is relative to wild-type Φ29 polymerase; see U.S. patent application Ser. No. 11/645,223, previously incorporated herein by reference in its entirety for all purposes.

As will be appreciated, the numbering of amino acid residues is with respect to the wild-type sequence of the Φ29 polymerase, and actual position within a molecule of the invention may vary based upon the nature of the various modifications that the enzyme includes relative to the wild type Φ29 enzyme, e.g., deletions and/or additions to the molecule, either at the termini or within the molecule itself. For the sequence of the wild-type Φ29 polymerase, see SEQ ID NO:1 in Table 3 hereinbelow.

Affinity Tags and Other Optional Polymerase Features

The modified recombinant DNA polymerase optionally includes additional features exogenous or heterologous to the polymerase. For example, the modified recombinant polymerase optionally includes one or more exogenous affinity tags, e.g., purification or substrate binding tags, such as a 6 His tag sequence, a GST tag, an HA tag sequence, a plurality of 6 His tag sequences, a plurality of GST tags, a plurality of HA tag sequences, or the like. These and other features useful in the context of binding a polymerase to a surface are optionally included, e.g., to orient and/or protect the polymerase active site when the polymerase is bound to a surface. Other useful features include recombinant dimer domains of the enzyme, and, e.g., large extraneous polypeptide domains coupled to the polymerase distal to the active site. For example, for Φ29, the active site is in the C terminal region of the protein, and added surface binding elements (extra domains, His Tags, etc.) are typically located in the N-terminal region to avoid interfering with the active site when the polymerase is coupled to a surface.

In general, surface binding elements and purification tags that can be added to the polymerase (recombinantly or, e.g., chemically) include, e.g., polyhistidine tags (such as 6 His tags), biotin, avidin, GST sequences, BiTag sequences, S tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Additional details on fixing a polymerase to a surface are found in U.S. patent application Ser. No. 11/645,135 "Protein engineering strategies to optimize activity of surface attached proteins" by Hanzel et al. and U.S. patent application Ser. No. 11/645,125 "Active surface coupled polymerases" by Hanzel et al., both filed Dec. 21, 2006 and incorporated herein by reference for all purposes.

Making and Isolating Recombinant Polymerases

Generally, nucleic acids encoding a modified recombinant polymerase of the invention can be made by cloning, recombination, in vitro synthesis, in vitro amplification and/or other available methods. A variety of recombinant methods can be used for expressing an expression vector that encodes a polymerase of the invention, e.g., a mutant polymerase that has an increased residence time for a nucleotide analogue. Recombinant methods for making nucleic acids, expression and isolation of expressed products are described, e.g., in Sambrook, Ausubel and Innis.

In addition, a plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, Gene 8:81 (1979); Roberts, et al., Nature, 328:731 (1987); Schneider, B., et al., Protein Expr. Purif. 6435:10 (1995); Ausubel, Sambrook, Berger (above). A catalogue of bacteria and bacteriophages useful for cloning is provided, e.g., by the ATCC, e.g., *The ATCC Catalogue of Bacteria and Bacteriophage* published yearly by the ATCC. Additional basic procedures for sequencing, cloning and other aspects of molecular biology and underlying theoretical considerations are also found in Watson et al. (1992) *Recombinant DNA Second Edition*, Scientific American Books, NY.

In addition, systems of orthogonal components are available that can incorporate any of a variety of unnatural amino acids into a recombinant protein (e.g., polymerase of the invention). In brief, a cell or other translation system (e.g., an in vitro translation system) is constructed that includes an orthogonal tRNA ("OtRNA"; a tRNA not recognized by the cell's endogenous translation machinery, such as an amber or 4-base tRNA) and an orthogonal tRNA synthetase ("ORS"; this is a synthetase that does not aminoacylate any endogenous tRNA of the cell, but which can aminoacylate the OtRNA in response to a selector codon). A nucleic acid encoding the enzyme is constructed to include a selector codon at a selected that is specifically recognized by the OtRNA. The ORS specifically incorporates an unnatural amino acid with a desired chemical functionality at one or more selected site(s) (e.g., distal to the active site). This chemical functional group can be unique as compared to those ordinarily found on amino acids, e.g., that incorporate keto or other functionalities. These are coupled to the coupling domains through appropriate chemical linkages. Further information on orthogonal systems can be found, e.g., in Wang et al., (2001), Science 292:498-500; Chin et al., (2002) Journal of the American Chemical Society 124:9026-9027; Chin and Schultz, (2002), Chem Bio Chem 11:1135-1137; Chin, et al., (2002), PNAS United States of America 99:11020-11024; and Wang and Schultz, (2002), Chem. Comm., 1-10. See also, International Publications WO 2002/086075, entitled "Methods and compositions for the production of orthogonal tRNA aminoacyl-tRNA synthetase pairs;" WO 2002/085923, entitled "In vivo incorporation of unnatural amino acids;" WO 2004/094593, entitled "Expanding the eukaryotic genetic code;" WO 2005/019415, filed Jul. 7, 2004; WO 2005/007870, filed Jul. 7, 2004; and WO 2005/007624, filed Jul. 7, 2004.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

In addition, essentially any nucleic acid can be custom or standard ordered from any of a variety of commercial sources, such as Operon Technologies Inc. (Alameda, Calif.).

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods. 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

Kits

The present invention also provides kits that incorporate the polymerases of the invention, e.g., with one or more nucleotide analogues, e.g., for sequencing, nucleic acid amplification, or the like. Such kits can include a polymerase of the invention packaged in a fashion to enable use of the polymerase, a set of different nucleotide analogues of the invention, e.g., those that are analogous to A, T, G, and C, e.g., where at least one of the analogues bears a detectable moiety, and in preferred aspects more than one, and in many cases, each, bears a detectably different labeling group, optionally to permit identification in the presence of the other analogues. Optionally the polymerase is a modified recombinant polymerase (e.g., a modified recombinant Φ29-type polymerase) and/or the set of nucleotide analogues includes one or more α-thiophosphate analogues. Depending upon the desired application, the kits of the invention optionally include additional reagents, such as natural nucleotides, a control template, and other reagents, such as buffer solutions and/or salt solutions, including, e.g., divalent metal ions, i.e., $Mg^{++}$, $Mn^{++}$ and/or $Fe^{++}$, standard solutions, e.g., dye standards for detector calibration. Such kits also typically include instructions for use of the compounds and other reagents in accordance with the desired application methods, e.g., nucleic acid sequencing, amplification and the like.

Nucleic Acid and Polypeptide Sequence and Variants

As described herein, the invention provides polynucleotide sequences encoding, e.g., a polymerase as described herein. Examples of polymerase sequences having mutations introduced to increase residence time are found herein, e.g., with reference to the specific mutation(s) relative to the wild-type polymerase. For example, any of the variety of mutations described herein can be introduced into wild-type Φ29 polymerase or a Φ29 polymerase bearing an N62D mutation (see, e.g., SEQ ID NO:1 herein and SEQ ID NO: 2 of U.S. patent application Ser. No. 11/645,223 for wild-type and N62D Φ29 polymerase sequences, respectively). However, one of skill in the art will immediately appreciate that the invention is not limited to those sequences. For example, one of skill will appreciate that the invention also provides, e.g., many related sequences with the functions described herein, e.g., polynucleotides and polypeptides encoding conservative variants of such polymerases.

Accordingly, the invention provides a variety of polypeptides (polymerases) and polynucleotides (nucleic acids that encode polymerases). A polynucleotide of the invention optionally includes any polynucleotide that encodes a modified recombinant polymerase described herein. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes an altered feature stabilizing the closed complex of the modified recombinant polymerase).

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant feature that increases residence time, e.g., by stabilizing the closed complex (for example, the conservative substitution can be of a residue distal to the active site region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitution within a group is a "conservative substitution".

TABLE A

Conservative Amino Acid Substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention. In addition, target nucleic acids which hybridize to a nucleic acid of the invention under high, ultra-high and ultra-ultra high stringency conditions, where the nucleic acids are other than a naturally occurring Φ29, or an N62D mutant, are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel supra; Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid that encodes a modified recombinant polymerase of the invention. The unique subsequence may be unique as compared to a nucleic acid corresponding to wild type Φ29, or to an N62D mutation thereof. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a modified recombinant polymerase of the invention. Here, the unique subsequence is unique as compared to, e.g., wild type Φ29, or to an N62D mutation thereof.

The invention also provides for target nucleic acids which hybridize under stringent conditions to a unique coding oligonucleotide which encodes a unique subsequence in a polypeptide selected from the sequences of the modified recombinant polymerases described herein, wherein the unique subsequence is unique as compared to a polypeptide corresponding to wild type Φ29, or to an N62D mutation (e.g., parental sequences from which polymerases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of polymerases) refers to two or more sequences or subsequences that have at least about 60%, about 80%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, at least about 500 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available. Genes (or proteins) that are homologous are referred to as homologs. Optionally, homologous proteins demonstrate comparable activities (e.g., polymerase activity or similar). "Orthologs" are genes in different species that evolved from a common ancestral gene by speciation. Normally, orthologs retain the same or similar function in the course of evolution. As used herein "orthologs" are included in the term "homologs."

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2007).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Determination of Residence Times for Nucleotide Analogues

The following sets forth a series of experiments that demonstrate determination of the residence times of a tetraphosphate nucleotide analogue and the corresponding α-thiophosphate nucleotide analogue.

Figure 5:
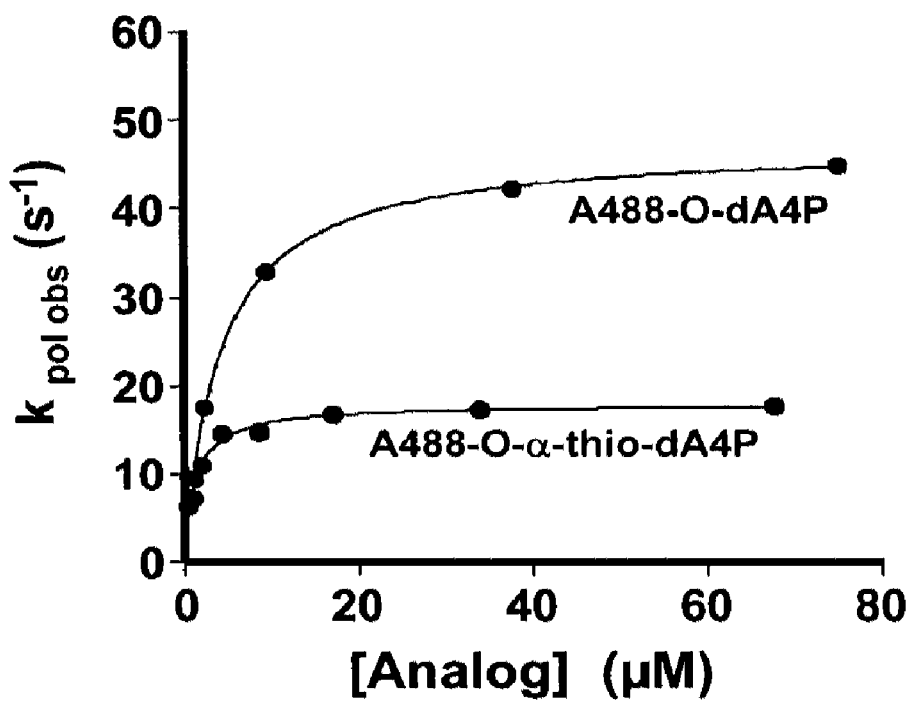
FIG. 5 presents a graph of reaction rates plotted against analogue concentration for analogues A488-O-dA4P and A488-O-α-thio-dA4P.

Single nucleotide incorporation assays were performed using a quench flow apparatus and a D12A modified Φ29 polymerase. Assays were performed for various concentrations of either A488-O-dA4P or A488-O-α-thio-dA4P. Reaction times were controlled by rapid addition of an EDTA quench solution. Reactants and products were separated on a 17% polyacrylamide gel. Product amounts were quantified on a Typhoon™ fluorescence scanner utilizing a Cy5-dye attached to the 5'-end of the primer. Rates for each reaction were determined by exponential fits to the data. As shown in FIG. 5, these rates were plotted versus the concentration of analogue to determine the intrinsic incorporation rate ($k_{pol}$) for reactions utilizing either A488-O-dA4P (upper curve) or A488-O-α-thio-dA4P (lower curve). Lower limit residence times were determined by taking the reciprocal values for the intrinsic $k_{pol}$ values. A summary of the results is shown in Table 2.

TABLE 2

Kinetic parameters determined from single nucleotide incorporation assays.

| Analog | $K_m$ | $k_{pol}$ | Residence Time (Lower Limit) |
|---|---|---|---|
| A488-O-α-thio-dA4P | 1.3 μM | 18 s$^{-1}$ | 56 ms |
| A488-O-dA4P | 4.1 μM | 47 s$^{-1}$ | 21 ms |

Example 2

Exemplary PHI29 Sequence

TABLE 3

Wild-type Φ29 amino acid sequence.

```
SEQ    mkhmprkmys cdfetttkve dcrvwaygym niedhseyki
ID     gnsldefmaw vlkvqadlyf hnlkfdgafi inwlerngfk
NO:    wsadglpnty ntiisrmgqw ymidiclgyk gkrkihtviy
1      dslkklpfpv kkiakdfklt vlkgdidyhk erpvgykitp
       eeyayikndi qiiaealliq fkqgldrmta gsdslkgfkd
       iittkkfkkv fptlslgldk evryayrggf twlndrfkek
       eigegmvfdv nslypaqmys rllpygepiv fegkyvwded
       yplhiqhirc efelkegyip tiqikrsrfy kgneylkssg
       geiadlwlsn vdlelmkehy dlynveyisg lkfkattglf
       kdfidkwtyi kttsegaikq laklmlnsly gkfasnpdvt
       gkvpylkeng algfrlgeee tkdpvytpmg vfitawaryt
       titaaqacyd riiycdtdsi hltgteipdv ikdivdpkkl
       gywahestfk rakylrqkty iqdiymkevd gklvegspdd
       ytdikfsvkc agmtdkikke vtfenfkvgf srkmkpkpvq
       vpggvvlvdd tftik
```

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising: a modified recombinant Φ29-type DNA polymerase, which modified recombinant polymerase comprises an amino acid sequence that is at least 90% identical to SEQ ID NO:1 and comprises an amino acid substitution at position 368 and an amino acid substitution at position 512, wherein numbering of positions is relative to SEQ ID NO:1, wherein the modified recombinant Φ29-type DNA polymerase exhibits polymerase activity; and
    a nucleotide analogue that is labeled on a phosphate group, wherein the base moiety of the analogue is selected from the group consisting of adenine, thymine, guanine, and cytidine.

2. The composition of claim 1, wherein the modified recombinant Φ29-type DNA polymerase is a modified recombinant Φ29 or PZA polymerase.

3. The composition of claim 1, wherein the modified recombinant polymerase comprises one or more amino acid substitutions selected from the group consisting of: T368D, T368E, K512D, and K512E.

4. The composition of claim 1, wherein the modified recombinant polymerase comprises at least one amino acid substitution or combination of substitutions selected from the group consisting of: K135D, K135E, T372D, T372E, T372R, T372K, K478D, K478E, K478R, L480K, L480R, T368D and L480K, T368E and L480K, T372D and K478R, T372E and K478R, T372R and K478D, T372R and K478E, T372K and K478D, and T372K and K478E.

5. The composition of claim 1, wherein the modified recombinant polymerase comprises at least one mutation relative to the corresponding wild-type polymerase that stabilizes the closed conformation of the modified recombinant polymerase.

6. The composition of claim 1, wherein the nucleotide analogue is labeled on the phosphate group with a fluorophore.

7. The composition of claim 1, wherein the nucleotide analogue has 4, 5, or 6 phosphate groups.

8. The composition of claim 1, comprising a DNA template, wherein the modified recombinant polymerase incorporates the nucleotide analogue into a copy nucleic acid in response to the DNA template.

9. The composition of claim 1, wherein the composition is present in a DNA sequencing system.

10. The composition of claim 9, wherein the sequencing system comprises a zero mode waveguide.

11. A method of sequencing a DNA template, the method comprising:
  a) providing a reaction mixture comprising:
    the DNA template,
    a replication initiating moiety that complexes with or is integral to the template,
    a modified recombinant Φ29-type DNA polymerase capable of replicating at least a portion of the template using the moiety in a template-dependent polymerization reaction, wherein the modified recombinant polymerase comprises an amino acid sequence that is at least 90% identical to SEQ ID NO:1 and comprises an amino acid substitution at position 368 and an amino acid substitution at position 512, wherein numbering of positions is relative to SEQ ID NO:1, and wherein the modified recombinant Φ29-type DNA polymerase exhibits polymerase activity, and
    one or more nucleotide analogues, each of which nucleotide analogues is labeled on a phosphate group, wherein the base moiety of each of the analogues is selected from the group consisting of adenine, thymine, guanine, and cytidine;
  b) subjecting the reaction mixture to a polymerization reaction in which the modified recombinant polymerase replicates at least a portion of the template in a template-dependent manner, whereby the one or more nucleotide analogues are incorporated into the resulting DNA; and
  c) identifying a time sequence of incorporation of the one or more nucleotide analogues into the resulting DNA.

12. The method of claim 11, wherein the one or more nucleotide analogues comprise first and second nucleotide analogues that comprise different labels which are distinguished from each other during the identifying step.

13. The method of claim 12, wherein the labels are fluorophores.

14. The method of claim 11, wherein the modified recombinant Φ29-type DNA polymerase is a modified recombinant Φ29 or PZA polymerase.

15. The method of claim 11, wherein the modified recombinant polymerase comprises one or more amino acid substitutions selected from the group consisting of: T368D, T368E, K512D, and K512E.

16. The method of claim 11, wherein the modified recombinant polymerase comprises at least one amino acid substitution or combination of substitutions selected from the group consisting of: K135D, K135E, T372D, T372E, T372R, T372K, K478D, K478E, K478R, L480K, L480R, T368D and L480K, T368E and L480K, T372D and K478R, T372E and K478R, T372R and K478D, T372R and K478E, T372K and K478D, and T372K and K478E.

17. The method of claim 11, wherein each of the nucleotide analogues has 4, 5, or 6 phosphate groups.

18. The method of claim 11, wherein the subjecting and identifying steps are performed in a zero mode waveguide.

19. A method of making a DNA, the method comprising:
  a) providing a reaction mixture comprising:
    a template,
    a replication initiating moiety that complexes with or is integral to the template,
    a modified recombinant Φ29-type polymerase capable of replicating at least a portion of the template using the moiety in a template-dependent polymerase reaction, wherein the modified recombinant polymerase comprises an amino acid sequence that is at least 90% identical to SEQ ID NO:1 and comprises an amino acid substitution at position 368 and an amino acid substitution at position 512, wherein numbering of positions is relative to SEQ ID NO:1, and wherein the modified recombinant Φ29-type DNA polymerase exhibits polymerase activity, and
    one or more nucleotide analogues, each of which nucleotide analogues is labeled on a phosphate group, wherein the base moiety of each of the analogues is selected from the group consisting of adenine, thymine, guanine, and cytidine; and b) reacting the mixture such that the polymerase replicates at least portion of the template in a template-dependent manner, whereby the one or more nucleotide analogues are incorporated into the resulting DNA.

20. The method of claim 19, wherein the modified recombinant Φ29-type DNA polymerase is a modified recombinant Φ29 or PZA polymerase.

21. The method of claim 19, wherein the modified recombinant polymerase comprises at least one amino acid substitution or combination of substitutions selected from the group consisting of: K135D, K135E, K512D, K512E, T368D, T368E, T372D, T372E, T372R, T372K, K478D, K478E, K478R, L480K, L480R, T368D and L480K, T368E and L480K, T372D and K478R, T372E and K478R, T372R and K478D, T372R and K478E, T372K and K478D, and T372K and K478E.

22. The method of claim 19, wherein each of the nucleotide analogues has 4, 5, or 6 phosphate groups.

23. The method of claim 19, wherein the mixture is reacted in a zero mode waveguide.

24. The method of claim 19, the method comprising detecting incorporation of the one or more nucleotide analogues.

25. The composition of claim 1, wherein the modified recombinant polymerase exhibits a residence time for the nucleotide analogue that is greater than about 20 milliseconds.

* * * * *

SEQUENCE LISTING

<160> NUMBER OF SEQ ID NOS: 1

<210> SEQ ID NO 1
<211> LENGTH: 575
<212> TYPE: PRT
<213> ORGANISM: Bacteriophage phi-29

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
                100                 105                 110

Arg Lys Ile His Thr Val Ile Tyr Asp Ser Leu Lys Lys Leu Pro Phe
            115                 120                 125

Pro Val Lys Lys Ile Ala Lys Asp Phe Lys Leu Thr Val Leu Lys Gly
```

```
                130                 135                 140
Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
                180                 185                 190

Asp Ser Leu Lys Gly Phe Lys Asp Ile Thr Thr Lys Lys Phe Lys
                195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
                260                 265                 270

Gly Lys Tyr Val Trp Asp Glu Asp Tyr Pro Leu His Ile Gln His Ile
                275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
                340                 345                 350

Phe Lys Ala Thr Thr Gly Leu Phe Lys Asp Phe Ile Asp Lys Trp Thr
                355                 360                 365

Tyr Ile Lys Thr Thr Ser Glu Gly Ala Ile Lys Gln Leu Ala Lys Leu
                370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
                420                 425                 430

Ile Thr Ala Trp Ala Arg Tyr Thr Thr Ile Thr Ala Ala Gln Ala Cys
                435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
                500                 505                 510

Leu Val Glu Gly Ser Pro Asp Asp Tyr Thr Asp Ile Lys Phe Ser Val
                515                 520                 525

Lys Cys Ala Gly Met Thr Asp Lys Ile Lys Lys Glu Val Thr Phe Glu
                530                 535                 540

Asn Phe Lys Val Gly Phe Ser Arg Lys Met Lys Pro Lys Pro Val Gln
545                 550                 555                 560
```

```
                -continued
Val Pro Gly Gly Val Val Leu Val Asp Asp Thr Phe Thr Ile Lys
            565                 570                 575
```